US006537815B2

(12) United States Patent
Romeo

(10) Patent No.: US 6,537,815 B2
(45) Date of Patent: Mar. 25, 2003

(54) METHOD OF ALTERING THE EXPRESSION OF CSRB TO MODIFY THE PROPERTIES OF A CELL

(75) Inventor: Tony Romeo, Burlington, TX (US)

(73) Assignee: University of North Texas, Health Science Center at Fort Worth, Ft Worth, TX (US)

( * ) Notice: Subject to any disclaimer, the term of this patent is extended or adjusted under 35 U.S.C. 154(b) by 0 days.

(21) Appl. No.: 09/736,734

(22) Filed: Dec. 13, 2000

(65) Prior Publication Data

US 2002/0015983 A1 Feb. 7, 2002

Related U.S. Application Data

(63) Continuation of application No. 09/112,584, filed on Jul. 9, 1998, now Pat. No. 6,228,638
(60) Provisional application No. 60/052,372, filed on Jul. 11, 1997.

(51) Int. Cl.[7] .......................... C12N 15/63; C12N 5/02; C12N 15/67

(52) U.S. Cl. ....................................... 435/471; 435/375

(58) Field of Search ................................. 435/375, 471

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,816,567 | A | 3/1989 | Cabilly et al. |

FOREIGN PATENT DOCUMENTS

| | | |
|---|---|---|
| EP | 073657 A | 8/1982 |
| EP | 431523 A2 A3 | 6/1991 |
| WO | WO 95/04074 A | 2/1995 |

OTHER PUBLICATIONS

Abrahams et al. (1990). "Prediction of RNA Secondary Structure, Including Pseudoknotting, by Computer Simulation" *Nucl. Acids Res.* 18(10):3035–3044.
Altschul et al. (1990). "Basic Local Alignment Search Tool" *J. Mol. Biol.* 215(3):403–410.
Ausubel et al. (1987). *Current Protocols in Molecular Biology*, Greene Publishing Associates, Brooklyn, NY (Table of Contents).
Ausubel et al. (1989). *Current Protocols in Molecular Biology*, John Wiley & Sons, Inc., New York (Table of Contents).

Baecker et al. (1986). "Biosynthesis of Bacterial Glycogen. Primary Structure of *Escherchia Coli* 1,4–Alpha–D–Glucan:1,4–Alpha–D–Glucan 6–Alpha–D–(1, 4–Alpha–D–Glucano)–Transferase as Deduced from the Nucleotide Sequence of the glg B Gene" *J. Biol. Chem.* 261 (19):8738–8743.
Beaucage et al. (1981). "Deoxynucleoside phosphoramidites– a new class of key intermediates for deoxypolynucleotide synthesis" *Tetra. Letts.* 22:1859–1862.
Beavis et al. (1990). "Rapid, Sensitive Analysis of Protein Mixtures by Mass Spectrometry" *Proc. Natl. Acad. Sci. U.S.A.* 87(17):6873–6877.
Bohannon et al. (1991). "Stationary–Phase–Inducible "Gearbox" Promoters: Differential Effects of KatF Mutations and Role of Sigma 70" *J. Bacteriol.* 173(14):4482–4492.
Braun et al. (1988). "Immunogenic Duplex Nucleic Acids are Nuclease Resistant" J. Immunol. 141(6): 2084–2089.
Bridger et al. (1978). "RelA Gene Control of Bacterial Glycogen Synthesis" *Can. J. Biochem.* 56(6):403–406.
Brosius et al. (1984). "Regulation of Ribosomal RNA Promoters with a Synthetic Lac Operator" *Proc. Natl. Acad. Sci. USA* 81(22):6929–6933.
Bryan, J.K. (1977). "Molecular Weights of Protein Multimers from Polyacrylamide Gel Electrophoresis" *Anal. Biochem.* 78(2):513–519.
Chatterjee, A. et al. (1995). "Inactivation of rsmA Leads to Overproduction of Extracellular Pectinases, Cellulases, and Proteases in Erwinia Carotovora Subsp. Carotovora in the Absence of the Starvation/cell Density–Sensing Signal, N–93–Oxohexanoly)–L–Homoserine Lactone" *Appl. Environ. Microbiol.* 61(5):1959–1967.
Chaturvedi, S. et al. (1996). "Stabilization of Triple–Stranded Oligonucleotide Complexes: Use of Probes Containing Alternating Phosphodiester and Stereo–Uniform Cationic Phosphoramidate Linkages" *Nucleic Acids Res.* 24(12):2318–23.
Cui, Y. et al. (1995). "Identification of a Global Repressor Gene, rsmA, of Erwinia Carotovora Subsp. Carotovora that Controls Extracellular Enzymes, N–(3–Oxohexanoyl)–L–Homoserine Lactone, and Pathogenicity in Soft–Rotting Erwinia spp" *J. Bacteriol.* 177(17):5108–5115.
Deutscher, ed. (1990). Guide to Protein Purification, vol. 182 of *Methods in Enzymology* Academic Press, Inc., San Diego pp. v–viii (Table of Contents).

(List continued on next page.)

Primary Examiner—Terry McKelvey
(74) *Attorney, Agent, or Firm*—Morrison & Foerster LLP

(57) ABSTRACT

The invention includes the gene csrB, the RNA encoded thereby and methods of use thereof. csrB RNA binds to and antagonizes the ability of CsrA to down-regulate the production of certain metabolic products. This invention is also drawn to methods of using csrB polynucleotides, and combination of csrB polynucleotides and CsrA polypeptides and antibodies that bind to such combinations.

8 Claims, 9 Drawing Sheets

OTHER PUBLICATIONS

Dietzler, D.N. et al. (1977). "Regulation of ADP–glucose synthetase, the rate–limiting enzyme of bacterial glycogen synthesis, by the pleiotropic nucleotides ppGpp and pppGpp" *Biochem. Biophys. Res. Commun.* 77(4):1459–1467.

Dietzler, D.N. et al. (1979). "Contribution of Cyclic Adenosine 3':5'–Monophosphate to the Regulation of Bacterial Glycogen Synthesis in Vivo. Effect of Carbon Source and cyclic Adenosine 3':5'–Monophosphate on the Quantitative Relationship Between the Rate of Glycogen Synthesis and the Cellular Concentrations of Glucose 6–Phosphate and Fructose 1,6–Diphosphate in *Escherichia Coli*" *J. Biol. Chem.* 254(17):8308–8317.

Fiers, W. et al. (1978). "Complete Nucleotide Sequence of SV40 DNA" *Nature* 273(5658):113–120.

Fleischmann, R.D. et al. (1995). "Whole–Genome Random Sequencing and Assembly of Haemophilus Infleunzae Rd" *Science* 269(5223):496–512.

Fournié, G.J. (1996). "Detection of Nucleosome–IgG Immune Complexes in Ascites from Mice Transplanted with Anti–DNA Antibody–Secreting Hybridomas and in Plasma from MRL–lpr/lpr Mice." *Clin. Exp. Immunol.* 104(2): 236–240.

Fuqua, W.C. et al. (1994). "Quorum Sensing in Bacteria: the LuxR–LuxI Family of Cell Density–Responsive Transcriptional Regulators" *J. Bacteriol.* 176(2):269–275.

Goding (1986). Monoclonal Antibodies: Principles and Practice, 2d ed., Academic Press, New York pp. vii–ix (Table of Contents).

Godowski, P.J. et al. (1988). "Signal Transduction and Transcriptional Regulation by Glucocorticoid Receptor–LexA Fusion Proteins" *Science* 241 (4867):812–816.

Gui, G. et al. (1997). "Cloning of CsrB, a structural RNA which binds to and antagonizes the global regulatory protein CsrA." *Abs. Gen. Meeting Am. Soc Microbiol.* 97:301.

Gultyaev, A.P. (1991). "The Computer Simulation of RNA Folding Involving Pseudoknot Formation" *Nucl. Acids. Res.* 19(9):2489–2494.

Gultyaev, A.P. et al. (1995). "The Computer Simulation of RNA Folding Pathways Using a Genetic Algorithm" *J. Mol. Biol.* 250(1):37–51.

Harlow, E and Lane, D. (1988). *Antibodies: A Laboratory Manual,* CSH Laboratories pp. iii–ix (Table of Contents).

Hedrick, J.L. et al. (1977). "Size and Charge Isomer Separation and Estimation of Molecular Weights of Proteins by Disc Gel Electrophoresis" *Arch. Bioch. Biophys.* 126(1):155–164.

Hengge–Aronis, R. et al. (1992). "Identification and Molecular Analysis of glgS, a Novel Growth–Phase–Regulated and rpoS–Dependent Gene Involved in Glycogen Synthesis in *Escherichia coli*" *Mol. Microbiol.* 6(14):1877–1886.

Hewick, R.M. et al. (1981). "A Gas–Liquid Solid Phase Peptide and Protein Sequenator" *J. Biol. Chem.* 256(15):7990–7997.

Huse, W.D. et al. (1989). "Generation of a Large Combinatorial Library of the Immunoglobulin Repertoire in Phage Lambda" *Science* 246 (4935):1275–1281.

Innis et al., (eds.). (1990). *PCR Protocols: A Guide to Methods and Applications,* Academic Press: San Diego pp. v–x (Table of Contents).

Janknecht, R. et al. (1991). "Rapid and Efficient Purification of Native Histidine–Tagged Protein Expressed by Recombinant Vaccinia Virus" *Proc. Natl. Acad. Sci. USA* 88(20):8972–8976.

Kolter (1992). "Life and Death in Stationary Phase" *ASM news* 58:75–79.

Kruse, P.F. and Patterson, M.K., eds., (1973) Tissue Culture, Method and Applications, Academic Press: New York pp. v–xiii (Table of Contents).

Laemmli, U.K. (1970). "Cleavage of Structural Proteins During the Assembly of the Head of Bacteriophage T4" *Nature* 227(259):680–685.

Lange, R. et al. (1991). "Identification of a Central Regulator of Stationary–Phase Gene Expression in *Escherichia Coli*" *Mol. Microbiol.* 5(1):49–59.

Latimer, L.J. et al. (1995). "Specificity of Monoclonal Antibodies Produced Against Phosphorothioate and Ribo Modified DNAs" *Mol. Immunol.* 32(14–15): 1057–1064.

Leckie, M.P. et al. (1983). "Regulation of Bacterial Glycogen Synthesis. Stimulation of Glycogen Synthesis by Endogenous and Exogenous Cyclic Adenosine 3':5'–Monophosphate in *Escherichia Coli* and the Requirement for a Functional CRP Gene" *J. Biol. Chem.* 258(6):3813–3824.

Leckie, M.P. et al. (1985). "Independence of Cyclic AMP and relA Gene Stimulation of Glycogen Synthesis in Intact *Escherichia Coli* Cells" *J. Bacteriol.* 161(1):133–140.

Liu, M et al. (1997). "The RNA molecule CsrB binds to the global regulatory protein CsrA and antagonizes its activity in *Escherichia coli."* *J. Biol. Chem.* 272:17502–17510.

Liu, M.Y. et al. (1995). "The Product of the Pleiotropic *Escherichia Coli* Gene csrA Modulates Glycogen Biosynthesis Via Effects on mRNA Stability" *J. Bacteriol.* 177(10):2663–2672.

Matin, A. (1991). "The Molecular Basis of Carbon–Starvation–Induced General Resistance in *Escherichia Coli*" *Mol. Microbiol.* 5(1):3–10.

Matin, A. et al. (1989). "Genetic Basis of Starvation Survival in Nondifferentiating Bacteria" *Ann. Rev. Microbiol.* 43:293–316.

Matteucci et al. (1981). "Synthesis of deoxyoligonucleotides on a polymer support" *J. Am. Chem. Soc.* 103:3185–3191.

McMaster, G.K. et al. (1977). "Analysis of Single– and Double–Stranded Nucleic Acids on polyacrylamide and Agarose Gels by Using Glyoxal and Acridine Orange" *Proc. Natl. Acad Sci. U.S.A.* 74(11):4835–4838.

Metzger, D. et al. (1988). "The Human Oestrogen Receptor Functions in Yeast" *Nature* 334(6177):31–36.

Miller, J. (1972) *Experiments in Molecular Genetics,* Cold Spring Harbor Laboratory, Cold Spring Harbor, NY pp. xi–xvi (Table of Contents).

Morfeldt, E. et al. (1995). "Activation of Alpha–Toxin Translation in Staphylococcus Aureus by the Trans–Encoded Antisense RNA, RNAIII" *EMBO J.* 14(18):4569–4577.

Murata, H. et al. (1994). "Regulation of the Production of Extracellular Pectinase, Cellulase, and Protease in the Soft Rot Bacterium Erwinia Carotovora Subsp. Carotovora: Evidence That aepH of E. Carotovora Subsp. Carotovora 71 Activates Gene Expression in E. Carotovora Subsp. Carotovora, E. Carotovora Subsp. Atroseptica, and *Escherichia Coli*" *Appl. Environ. Microbiol.* 60(9):3150–3159.

Murayama et al. (1996). "Evidence for involvement of *Escherichia coli* genes pmbA, csrA and a previously unrecognized gene tldD, in the control of DNA gyrase by letD (ccdB) of sex factor F" *J. Mol. Biol.* 256:483–502.

Peyrottes, S. et al. (1996). "Oligodeoxynucleoside Phosphoramidates (P–NH2): Synthesis and Thermal Stability of Duplexes with DNA and RNA Targets" *Nucleic Acids Res.* 24(10): 1841–1848.

Platt, T. (1986). "Transcription Termination and the Regulation of Gene Expression" *Ann. Rev. Biochem.* 55:339–372.

Preiss, J. et al. (1989). "Physiology, Biochemistry and Genetics of Bacterial Glycogen Synthesis" *Adv. Microb. Physiol.* 30:183–238.

Putterman, C. et al. (1996). "The Double Edged Sword of the Immune Response: Mutational Analysis of a Murine Anti–Pneumococcal, Anti–DNA Antibody" *J. Clin. Invest.* 97(10):2251–2259.

Reines, D. (1991). "RNA Polymerase II Elongation Complex. Elongation Complexes Purified Using an Anti–RNA Antibody do not Contain Initiation Factor Alpha" *J. Biol. Chem.* 266(16):10510–10517.

Reizer et al., (1996). "Novel phosphotransferase–encoding genes revealed by analysis of the *Escherichia coli* genome: a chimeric gene encoding an Enzyme I homologue that possesses a putative sensory transduction domain" *Gene* 181(1–2):103–8.

Romeo et al. (1990). "Genetic regulation of glycogen biosynthesis in *Escherichic coli:* In vivo effects of the catabolite repression and stringent response systems in glg gene expression" *Curr. Microbiol.* 21:131–137.

Romeo, T. (1996). "Post–Transcriptional Regulation of Bacterial Carbohydrate Metabolism: Evidence that the Gene Product CsrA is a Global mRNA Decay Factor" *Res. Microbiol.* 147(6–7):505–512.

Romeo, T. et al. (1988). "Analysis of the *Escherichia coli* Glycogen Gene Cluster Suggests that Catabolic Enzymes are Encoded Among the Biosynthetic Genes" *Gene* 70(2):363–376.

Romeo, T. et al. (1989). "Genetic Regulation of Glycogen Biosynthesis in *Escherichia Coli:* in Vitro Effects of Cyclic AMP and Guanosine 5'–Diphosphate 3'–Diphosphate and Analysis of in Vivo Transcripts" *J. Bacteriol.* 171(5):2773–2782.

Romeo, T. et al. (1993). "Identification and Molecular Characterization of csrA, a Pleiotropic Gene from *Escherichia Coli* that Affects Glycogen Biosynthesis, Gluconeogenesis, Cell Size, and Surface Properties" *J. Bacteriol.* 175(15):4744–4755.

Romeo, T. et al. (1993). "Genetic and Physical Mapping of the Regulatory Gene csrA on the *Escherichia Coli* K–12 Chromosome" *J. Bacteriol.* 175(17):5740–5741.

Sabnis, N.A. et al. (1995). "Pleiotropic Regulation of Central Carbohydrate Metabolism in *Escherichia coli* Via the Gene csrA" *J. Biol. Chem.* 270(49):29096–29104.

Sambrook et al. (1989) *Molecular Cloning: A Laboratory Manual,* 2d. edition, Cold Spring Harbor Press, Cold Spring Harbor, New York pp. xi–xxxviii (Table of Contents).

Sanger, F. et al., (1977). "DNA Sequencing with Chain–Terminating Inhibitors" *Proc. Natl. Acad. Sci. USA* 74(12):5463–5467.

Schellhorn, H.E. et al. (1992). "Regulation of katF and katE in *Escherichia Coli* K–12 by Weak Acids" *J. Bacteriol.* 174(14):4769–4776.

Schmidt et al. (1945). "A method for the determination of desoxyribonucleic acid, ribonucleic acid, and phosphoproteins in animal tissues" *J. Biol. Chem.* 181:83–89.

Schöler, H.R. & Gruss, P. (1983). "Competition for cellular factors required for the transcriptional activation of enhancers" in *Current Communications in Molecular Biology: Enhancers and Eukaryotic Gene Expression.* pp. 16–20, Y.Gluzman and T.Shenk eds., Cold Spring Harbor: New York, pp. vii–x (Table of Contents).

Schultz, R.G. et al. (1996). "Olido–2'–Fluoro–2'–Deoxynucleotide N3'→P5' Phosphoramidates: Synthesis and Properties" *Nucleic Acids Res.* 24(15): 2966–2973.

Scopes, R.L. (1982). *Protein Purification: Principles and Practics, 2nd ed.* Springer–Verlag: New York pp. xiii–xv (Table of Contents).

Shimoike, T. et al. (1995). "Product of a New Gene, Syd, Functionally Interacts with SecY When Overproduced in *Escherichia coli" J. Biol. Chem.* 270(10):5519–5526.

Shine, J. et al. (1974). "The 3'Terminal Sequence of *Escherichia coli* 16S Ribosomal RNA: Complementarity to Nonsense Triplets and Ribosome Binding Sites" *Proc. Natl. Acad. Sci. USA* 71(4):1342–1346.

Siegele, D.A. et al. (1992) "Life after Log" *J. Bacteriol.* 174(2):345–348.

Sledjeski,D. et al. (1995). "A Small RNA Acts as an Antisilencer of the H–NS–Silenced rcsA Gene of *Escherichia Coli" Proc. Natl. Acad. Sci. USA* 92(6):2003–2007.

Smith, P.K. et al. (1985). "Measurement of Protein Using Bicinchoninic Acid" *Anal Biochem.* 150(1):76–85.

Sogo et al. (1987). "Binding of protein to nucleic acids" In *Electron Microscopy In Molecular Biology, A Practical Approach,* Sommerville et al., eds., IRL Press: Oxford, pp. 61–79.

Swift, S. et al. (1996). "Quorum Sensing: a Population–Density Component in the Determination of Bacterial Phenotype" *TIBS* 21(6):214–219.

Taguchi, M. et al. (1980). "Augmentation of Glycogen Synthesis Under Stringent Control in *Escherichia Coli" J. Biochem.* 88(2):379–387.

Thiry, M. (1993). "Differential Location of Nucleic Acids Within Interchromatin Granule Clusters" *Eur. J. Cell. Biol.* 62(2): 259–69.

Thiry, M. (1994). "Cytochemical and Immunocytochemical Study of Coiled Bodies in Different Cultured Cell Lines" *Chromosoma* 103(4): 268–276.

Towbin, H. et al. (1979). "Electrophoretic Transfer of Proteins from Polyacrylamide Gels to Nitrocellulose Sheets: Procedure and Some Applications" *Proc. Natl. Acad. Sci. U.S.A.* 76(9):4350–4354.

Vasina, J.A. et al. (1996). "Recombinant Protein Expression at Low Temperatures Under the Transcriptional Control of the Major *Escherichia Coli* Cold Shock Promoter cspA" *Appl. Environ. Microbiol.* 62(4): 1444–1447.

Wahl et al. (1987) *Methods in Enzymology,* vol. 152:399–407, 415–423, Academic Press, Inc., San Diego, 1987.

White, D. et al. (1996). "Phylogenetic Distribution of the Global Regulatory Gene csrA Among Eubacteria" *Gene* 182(1–2):221–223.

Yang, H. et al. (1996). "Coordinate Genetic Regulation of Glycogen Catabolism and Biosynthesis in *Escherichia Coli* via the CsrA Gene Product" *J. Bacteriol.* 178(4):1012–1017.

Yanisch–Perron et al. (1985). "Improved M13 Phage Cloning Vectors And Host Strains: Nucleotide Sequences of the M13mp18 and pUC19 Vectors" *Gene 33:*103–119.

Yu, F. et al. (1988). "Alpha–Glucan Phosphorylase from *Escherichia Coli,* Cloning of the Gene, and Purification and Characterization of the Protein" *J. Biol. Chem.* 263(27):13706–13711.

```
                syd
K-12    TAATCCAAATACCCCATCTGGTTGTGAGAGATCTCTTACAGACTCTGTAGGAGATCGCCA        60

K-12    GGAAATAAGCGAATACTTAAAAAGATAAGAATCGTTATTTTCATTTAAAATCAAAATGTT        120

* pCSRB-S
K-12    GATTGTTAATTCTTAACTTTCATATGAAATTTTCCTTAAGGCATTGTCTGTAAGCGCCTT        180

5'end CsrB cDNA *
K-12    GTAAGACTTCGCGAAAAAGACGATTCTATCTTCGTCGACAGGGAGTCAGACAACGAAGTG        240

K-12    ...AACATCAGGATGATGACACTTCTGCAGGACACACCAGGATGGTGTTTCAGGGAAAGGCTT     300

K-12    CTGGATGAAGCGAAGAGGATGACGCAGGACGCGTTAAAGGACACCTCCAGGATGGAGAAT        360

K-12    GAGAACCGGTCAGGATGATTCGGTGGGTCAGGAAGGC.CAGGGACAC..TTCAGGATGAAGTA    420

K-12    TCACATCGGGGTGGTGTGAGCAGGAAGCAATAGTTCAGGATGAACGATTGGCCGCAAGGC      480

K-12    CAGAGGAAAAGTTGTCAAGGATGAGCAGGGAGCAACAAAAGTAGCTGGAATGCTGCGAAA      540

3'end CsrB cDNA *
K-12    CGAACCGGGAGCGCTGTGAATACAGTGCTCCCTTTTTTTATTCCTGCTATCCTTCGCGGC      600 pCSRB-S *
K-12    AGTTTTTCTTATTGAGGTTGCTTTATGACCACTCATGACCGCGTTCGTCTCCAG             654
```

Figure 1

```
                syd
K-12    TAATCCAAATACCCCATCTGGTTGTGAGAGATCTCTTACAGACTCTGTAGGAGATCGCCA        60
E.car   tagttaattataataaaaatccgcagtgtcactgatggggtgttgagaaacactgtcaat        60

K-12    GGAAATAAGCGAATACTTAAAAAGATAAGAATCGTTATTTTCATTTAAAATCAAAATGTT       120
E.car   taccccttgctgaaagctgacttaatacatcttattacttaagttagtaaccggttacag       120
                                                        * pCSRB-S
K-12    GATTGTTAATTCTTAACTTTCATATGAAATTTTCCTTAAGGCATTGTCTGTAAGCGCCTT       180
E.car   tgtgtgtaacagttactataggtaacaaaataacgttactgcactcgggttgttttcagg       180
                            5'end CsrB cDNA *
K-12    GTAAGACTTCGCGAAAAAGACGATTCTATCTTCGTCGACAGGGAGTCAGACAACGAAGTG       240
E.car   aagaaacattgtttcaggaagaggcattgtttttaggaagaaacgctgttttaaggataaa       240

K-12    ...AACATCAGGATGATGACACTTCTGCAGGACACACCAGGATGGTGTTTCAGGGAAAGGCTT    300
E.car   catcgtttttaggaagaaacgatcgtttcaggaagaagcgttgttttcaggaagaagaacg       300

K-12    CTGGATGAAGCGAAGAGGATGACGCAGGACGCGTTAAAGGACACCTCCAGGATGGAGAAT       360
E.car   .gttttcaggaagaaacatggttttcaggatgaaatcagggacacctccaggaaggagacc       359

K-12    GAGAACCGGTCAGGATGATTCGGTGGGTCAGGAAGGC.CAGGGACAC..TTCAGGATGAAGTA   420
E.car   gagagccgattaggaata.tcggtgggcaggagcctaaagggattgaatcacggaagatac   420

K-12    TCACATCGGGGTGGTGTGAGCAGGAAGCAATAGTTCAGGATGAACGATTGGCCGCAAGGC       480
E.car   aggatggacacgtcaggaagaaagtgggacgccagcaaggattgtgggttaggacgacca       480

K-12    CAGAGGAAAAGTTGTCAAGGATGAGCAGGGAGCAACAAAAGTAGCTGGAATGCTGCGAAA       540
E.car   aaaaggaaaagttttcacggatgagcagggatgcaaatgtgtagcgggatagctataaaa       540
                            3'end CsrB cDNA *
K-12    CGAACCGGGAGCGCTGTGAATACAGTGCTCCCTTTTTTTATTCCTGCTATCCTTCGCGGC       600
E.car   cgaaccgggggtactgagtaatcagtacccccaattttttt
                                                        pCSRB-S *
K-12    AGTTTTTCTTATTGAGGTTGCTTTATGACCACTCATGACCGCGTTCGTCTCCAG            654
```

Figure 9

SEQUENCE LISTING

<160> NUMBER OF SEQ ID NOS: 10

<210> SEQ ID NO 1
<211> LENGTH: 654
<212> TYPE: DNA
<213> ORGANISM: Escherichia coli

<400> SEQUENCE: 1

```
taatccaaat accccatctg gttgtgagag atctcttaca gactctgtag gagatcgcca      60
ggaaataagc gaatacttaa aaagataaga atcgttattt tcatttaaaa tcaaatgtt     120
gattgttaat tcttaactt catatgaaat tttccttaag gcattgtctg taagcgcctt     180
gtaagacttc gcgaaaaaga cgattctatc ttcgtcgaca gggagtcaga caacgaagtg     240
aacatcagga tgatgacact tctgcaggac acaccaggat ggtgtttcag ggaaaggctt     300
ctggatgaag cgaagaggat gacgcaggac gcgttaaagg acacctccag gatggagaat     360
gagaaccggt caggatgatt cggtgggtca ggaaggccag ggacacttca ggatgaagta     420
tcacatcggg gtggtgtgag caggaagcaa tagttcagga tgaacgattg gccgcaaggc     480
cagaggaaaa gttgtcaagg atgagcaggg agcaacaaaa gtagctggaa tgctgcgaaa     540
cgaaccggga gcgctgtgaa tacagtgctc cctttttta ttcctgctat ccttcgcggc     600
agttttttctt attgaggttg ctttatgacc actcatgacc gcgttcgtct ccag          654
```

<210> SEQ ID NO 2
<211> LENGTH: 359
<212> TYPE: RNA
<213> ORGANISM: Escherichia coli

<400> SEQUENCE: 2

```
gagucagaca acgaagugaa caucaggaug augacacuuc ugcaggacac accaggaugg      60
uguuucaggg aaaggcuucu ggaugaagcg aagaggauga cgcagacgcg uuaaaggaca     120
ccuccaggau ggagaaugag aaccggucag gaugauucgg ugggucagga aggccaggga     180
cacuucagga ugaaguauca caucggggug gugugagcag gaagcaauag uucaggauga     240
acgauuggcc gcaaggccag aggaaaaguu gucaaggaug agcagggagc aacaaaagua     300
gcuggaaugc ugcgaaacga accgggagcg cugugaauac agugcucccu uuuuuauu      359
```

<210> SEQ ID NO 3
<211> LENGTH: 580
<212> TYPE: DNA
<213> ORGANISM: Escherichia coli

<400> SEQUENCE: 3

```
tagttaatta taataaaaat ccgcagtgtc actgatgggg tgttgagaaa cactgtcaat      60
taccccttgc tgaaagctga cttaatacat cttattactt aagttagtaa ccggttacag     120
tgtgtgtaac agttactata ggtaacaaaa taacgttact gcactcgggt tgttttcagg     180
aagaaacatt gtttcaggaa gaggcattgt tttaggaaga acgctgtttt taaggataaa     240
catcgtttta ggaagaaacg atcgtttcag gaagaagcgt tgttttcagg aagaagaacg     300
gttttcagga agaaacatgg tttcaggatg aaatcaggga cacctccagg aaggagaccg     360
agagccgatt aggaatatcg gtggggcagg agcctaaagg gattgaatca cggaagatac     420
aggatggaca cgtcaggaag aaagtgggac gccagcaagg attgtggtt aggacgacca     480
aaaggaaaa gttttcacgg atgagcaggg atgcaaatgt gtagcgggat agctataaaa     540
```

```
cgaaccgggg gtactgagta atcagtaccc ccaatttttt                              580

<210> SEQ ID NO 4
<211> LENGTH: 20
<212> TYPE: DNA
<213> ORGANISM: Escherichia coli

<400> SEQUENCE: 4
atgctgattc tgactcgtcg                                                    20

<210> SEQ ID NO 5
<211> LENGTH: 40
<212> TYPE: DNA
<213> ORGANISM: Escherichia coli

<400> SEQUENCE: 5
ttaatgatga tgatgatgat ggtaactgga ctgctgggat                              40

<210> SEQ ID NO 6
<211> LENGTH: 15
<212> TYPE: PRT
<213> ORGANISM: Escherichia coli

<400> SEQUENCE: 6

Met Leu Ile Leu Thr Arg Arg Val Gly Glu Thr Leu Met Ile Gly
 1               5                  10                  15

<210> SEQ ID NO 7
<211> LENGTH: 11
<212> TYPE: PRT
<213> ORGANISM: Rabbit

<400> SEQUENCE: 7

Lys Glu Val Ser Val His Arg Glu Glu Ile Tyr
 1               5                  10

<210> SEQ ID NO 8
<211> LENGTH: 10
<212> TYPE: RNA
<213> ORGANISM: Escherichia coli

<400> SEQUENCE: 8
uuuuuuuauu                                                               10

<210> SEQ ID NO 9
<211> LENGTH: 21
<212> TYPE: DNA
<213> ORGANISM: Escherichia coli

<400> SEQUENCE: 9
gtaagcgcct tgtaagactt c                                                  21

<210> SEQ ID NO 10
<211> LENGTH: 21
<212> TYPE: DNA
<213> ORGANISM: Escherichia coli

<400> SEQUENCE: 10
ctggagacga acgcggtcat g                                                  21
```

METHOD OF ALTERING THE EXPRESSION OF CSRB TO MODIFY THE PROPERTIES OF A CELL

CROSS REFERENCE TO RELATED APPLICATIONS

This application is a continuation of U.S. Ser. No. 09/112,584, filed Jul. 9, 1998, now U.S. Pat. No. 6,228,638 which claims the benefit of U.S. Provisional Application Ser. No. 60/052,372, filed Jul. 11, 1997, the disclosures of which are incorporated herein by reference in their entirety.

STATEMENT OF RIGHTS TO INVENTIONS MADE UNDER FEDERALLY SPONSORED RESEARCH

This invention was made with government support under grant numbers MCB 9218796 and BIR 9413907 from the National Science Foundation, and AI 40187 from the National Institutes of Health. The government has certain rights in the invention.

TECHNICAL FIELD

This invention is related to the field of microbiology. Specifically, the invention relates to alteration of metabolic pathways in E. coli and other bacteria.

BACKGROUND ART

Bacteria grown in the laboratory have three stages of growth: the lag phase, in which little change in the number of viable cells occurs; the log phase, in which exponential increase in numbers occurs;.and the stationary phase, in which increase ceases. During the transition into stationary phase, bacteria acquire numerous new physiological properties which enhance their ability to compete and survive under suboptimal conditions. For reviews, see Kolter (1992) *ASM News* 58:75–79; Matin (1991) *Mol. Microbiol.* 5:3–10; Matin et al. (1989) *Ann. Rev. Microbiol.* 43:293–316; and Siegele et al. (1992) *J. Bacteriol.* 174:345–348. A few global regulatory factors mediate many of the extensive changes in gene expression that occur as E. coli enters the stationary phase. In E. coli, for example, the induction of several genes and operons requires a putative sigma factor known as rpoS or katF. Bohannon et al. (1991) *J. Bacteriol.* 173:4482–4492; Lange et al. (1991) *Mol. Microbiol.* 5:49–51; Matin (1991); and Schellhorn et al. (1992) *J. Bacteriol.* 174:4769–4776.

One of the metabolic pathways transcriptionally activated in stationary phase mediates glycogen biosynthesis. The accumulation of glycogen in the early stationary phase reflects at least two levels of control: allosteric regulation of the committed step of the biochemical pathway; and enhanced expression of the structural genes for the pathway. Expression of this pathway does not require rpoS for expression. Bohannon et al. (1991).

The essential enzymes of the glycogen pathway are glgC (encoding ADPglucose pyrophosphorylase [EC 2.7.7.27]) and glgA (encoding glycogen synthase [EC 2.4.1.21]), which are apparently cotranscribed in an operon, glgCAY. Romeo et al. (1990) *Curr. Microbiol.* 21:131–137; and Romeo et al. (1989) *J. Bacteriol.* 171:2773–2782. The operon also includes the gene glgY or glgP, which encodes the catabolic enzyme glycogen phosphorylase [E.C 2.4.1.1]. Romeo et al. (1988) *Gene* 70:363–376; and Yu et al. (1988) *J. Biol. Chem.* 263:13706–13711. Four stationary-phase-induced transcripts have been mapped within the 0.5 kb upstream noncoding region of the glgC gene from E. coli, implying a complex transcriptional regulation of glgCA.

Located upstream of glgCAY is another operon, glgBX, also encoding genes involved in the glycogen pathway. The gene glgB encodes glycogen branching enzyme [EC 2.4.1.18] and is transcribed independently of glgCA. Baecker et al. (1986) *J. Biol. Chem.* 261:8738–8743; Romeo et al. (1988); Preiss et al. (1989) *Adv. Microb. Physiol.* 30:183–233; and Romeo et al. (1989).

The gene csrA or "carbon storage regulator" is a trans-acting factor which effects potent negative regulation of glycogen biosynthesis. Romeo et al. (1993a) *J. Bacteriol.* 175:4744–4755; and Romeo et al. (1993b) *J. Bacteriol.* 175:5740–5741. CsrA is a global regulator which controls numerous genes and enzymes of carbohydrate metabolism. In E. coli K-12, it exerts pleiotropic effects, acting as a negative regulator of glycogen biosynthesis, gluconeogenesis and glycogen catabolism, as a positive factor for glycolysis, and affecting cell surface properties. Romeo et al. (1993a); Liu et al. (1995) *J. Bacteriol.* 177:2663–2672; Sabnis et al. (1995) *J. Biol. Chem.* 270:29096–29104; and Yang et al. (1996) *J. Bacteriol.* 178:1012–1017.

Csr is the third system discovered to be involved in the regulation of glgCA-mediated glycogen biosynthesis and the only one known to down-regulate the expression of this operon. The other two involve cyclic AMP (cAMP)/cAMP receptor protein and guanosine 3'-bisphosphate 5'-bisphosphate (ppGpp), which are positive regulators of glgCA. Romeo et al. (1990); Romeo et al. (1989); Bridger et al. (1978) *Can. J. Biochem.* 56:403–406; Dietzler et al. (1979) *J. Biol. Chem.* 254:8308–8317; Dietzler et al. (1977) *Biochem. Biophys. Res. Commun.* 77:1459–1467; Leckie et al. (1983) *J. Biol. Chem.* 258:3813–3824; Leckie et al. (1985) *J. Bacteriol.* 161:133–140; and Taguchi et al. (1980) *J. Biochem.* 88:379–387. The physiological role played by these three systems may be to establish an intrinsic metabolic capacity for glycogen synthesis in response to nutritional status. The effects of other regulatory factors, such as the allosteric effectors fructose-1,6-bisphosphate and AMP, may be superimposed upon this intrinsic metabolic capacity.

glgCA expression does not appear to be regulated by other global systems such as the nitrogen starvation system, mediated by NtrC and NtrA or $\sigma^{54}$; heat shock, mediated by $\sigma^{32}$; or the katF-dependent system. Preiss et al. (1989); Romeo et al. (1989); and Hengge-Aronis et al. (1992) *Mol. Microbiol.* 6:1877–1886.

A homolog of csrA in the pathogenic Erwinia species is rsmA (repressor of stationary phase metabolites). Chatterjee et al. (1995) *Appl. Environ. Microbiol.* 61:1959–1967; and Cui et al. (1995) *J. Bacteriol.* 177:5108–5115. rsmA has a role in the expression of several virulence factors of soft rot disease of higher plants, including pectinase, cellulase and protease activities. rsmA may also modulate the production of the quorum-sensing metabolite N-(3-oxohexanoyl)-L-homoserine lactone. Homologs of this metabolite are secreted by numerous Gram-negative bacteria, where they activate the expression of a variety of genes in response to cell density, as reviewed in Fuqua et al. (1994) *J. Bacteriol.* 176:269–275; and Swift et al. (1996) *TIBS* 21:214–219. Widespread phylogenetic distribution of csrA homologs among eubacteria points to a broad significance and ancient origin for this regulatory system in this group of organisms. White et al. (1.996) *Gene* 182:221–223; and Romeo (1996) *Res. Microbiol.* 147:505–512.

The csrA gene product or protein (CsrA) is a 61 amino acid protein containing a conserved RNA-binding motif and apparently mediates its regulatory activity via a cis-acting region located close to or overlapping the glgC ribosome binding site. Liu et al. (1995). CsrA strongly inhibits glycogen accumulation and affects the ability of cells to utilize certain carbon sources for growth. The down-regulated expression of csrA and CsrA can be useful for enhancing expression of products produced by alternative pathways. Such products include, but are not limited to, antibiotics, metabolites, organic acids, amino acids and a wide variety of industrially important compounds produced in bacterial fermentation systems.

As an example, down-regulating csrA expression can be used to increase the production of aromatic amino acids (e.g., tyrosine, phenylalanine, and tryptophan). These amino acids, which are commercially produced using *E. coli* cultures, have numerous uses, including the production of aspartame (Nutrisweet™). The TRI-5 mutation in csrA (csrA::kan$^R$) causes overexpression of the genes pckA [encoding phosphoenolpyruvate (PEP) carboxykinase] and pps (phosphoenolpyruvate synthase), thereby raising production of PEP. PEP is in turn a precursor of aromatic amino acids and other metabolic products.

Further "metabolic engineering" can lead to even greater yields of desired amino acids or other products. In addition to being an amino acid precursor, PEP is a precursor of glucose via gluconeogenesis. Glucose is, in turn, a precursor of glycogen. Gluconeogenesis and glycogen synthesis are elevated in csrA mutants and would compete for the synthesis of aromatic amino acids. Therefore, in order to further increase carbon flow into the desired products (e.g., amino acids), engineering of gluconeogenesis, glycogen biosynthesis and possibly other pathways is desirable. A mutation in fbp, which encodes fructose-1,6-bisphosphatase, prevents gluconeogenesis from proceeding beyond the synthesis of fructose-1,6-bisphosphate. A mutation in glgC (ADP-glucose pyrophosphorylase) or glgA (glycogen synthase) further blocks residual glucose or glucose derivatives obtained from the media or generated within the cell from being used for glycogen synthesis. Each of these mutations is already known and can be introduced into a cell by methods known in the art. Further enhancement of the synthesis of a single aromatic amino acid can be achieved by introducing mutations which block the synthesis of other amino acids.

Thus, CsrA can be utilized in the context of the biochemical pathways known in the art to increase expression of desired compounds in bulk bacterial cultures.

All of the literature and patents cited herein, supra and infra, are hereby incorporated herein by reference.

SUMMARY OF THE INVENTION

The invention encompasses the *E. coli* csrB gene and RNA encoded thereby. csrB RNA binds to the global regulatory protein CsrA and antagonizes its ability to down-regulate expression of metabolic products.

This invention also encompasses methods using the csrB gene and csrB RNA to modulate activity of CsrA and, in turn, to regulate expression of metabolic products in bacterial cultures.

This invention also encompasses compositions comprising csrB polynucleotides and fragments and derivatives thereof, in combination with CsrA polypeptides and fragments and derivatives thereof.

This invention also encompasses antibodies to csrB polynucleotides or complexes formed between csrB polynucleotides and CsrA polypeptides.

Accordingly, in one aspect, the invention provides an isolated csrB polynucleotide.

In one embodiment the invention provides the sequence of the polynucleotide with at least 70% identity to that depicted in FIG. 1 (SEQ ID NO:1), and which comprises at least one binding site for CsrA protein or a complement of a binding site for CsrA protein.

In another embodiment, the invention provides the polynucleotide depicted in FIG. 1 (SEQ ID NO: 1).

In another embodiment, the invention provides a composition comprising a csrB polynucleotide and CsrA wherein the ratio of csrB polynucleotide to CsrA is about 1:18.

In another embodiment, the invention provides a method of altering the metabolism or structural or functional properties of a cell comprising altering genetic expression or CsrA-binding activity of csrB.

In another embodiment, the invention provides a method of altering the metabolism or structural or functional properties of a cell by altering genetic expression or CsrA-binding activity of csrB, wherein CsrA-binding activity of csrB is altered by mutating csrB.

In another embodiment, the invention provides a method of altering the metabolism or structural or functional properties of a cell comprising altering genetic expression or CsrA-binding activity of csrB, wherein a result of altered genetic expression of csrB is a change in the level of production of a metabolic compound, wherein the level of production is at least partially regulated by CsrA.

In another embodiment, the invention provides a method of altering the metabolism or structural or functional properties of a cell comprising altering genetic expression or CsrA-binding activity of csrB, wherein a result of altered genetic expression of csrB is a change in glycogen biosynthesis or gluconeogenesis.

In another embodiment, the invention provides a method of altering the metabolism or structural or functional properties of a cell comprising altering genetic expression or CsrA-binding activity of csrB, wherein a result of altered genetic expression of csrB is a change in the level of production of a metabolic compound, wherein the level of production is at least partially regulated by CsrA, wherein the metabolic compound is an amino acid.

In another embodiment, the invention provides a method of altering the metabolism or structural or functional properties of a cell comprising altering genetic expression or CsrA-binding activity of csrB, wherein expression of the csrB gene is increased.

In another embodiment, the invention provides a method of altering the metabolism or structural or functional properties of a cell comprising altering genetic expression or CsrA-binding activity of csrB wherein expression of the csrB gene is decreased.

In another embodiment, the invention provides a method of altering the metabolism or structural or functional properties of a cell comprising altering genetic expression or CsrA-binding activity of csrB wherein expression of the csrB gene is under inducible control.

In another embodiment, the invention provides an antibody capable of binding to a composition comprising a CsrA and a csrB polynucleotide.

In another embodiment, the invention provides a method of modulating the level of production of a metabolic compound, wherein the level of production is at least partially regulated by CsrA, comprising the step of binding to CsrA an antibody capable of binding to a composition comprising CsrA and a csrB polynucleotide.

In another embodiment, the invention provides a vector comprising a csrB gene, further comprising a csrA gene In another embodiment, the invention provides a vector comprising a csrB gene, further comprising a csrA gene, wherein the csrB gene and csrA gene are controlled by different inducible promoters.

In another embodiment, the invention provides a method of modulating the level of production of a metabolic compound, wherein the level of production is at least partially controlled by CsrA, comprising introducing a vector comprising a csrB gene, further comprising a csrA gene, into a host cell; and raising the level of production of the metabolic compound by inducing expression of csrB.

In another embodiment, the invention provides a method of modulating the level of production of a metabolic compound, wherein the level of production is at least partially controlled by CsrA, comprising introducing a vector comprising a csrB gene, further comprising a csrA gene, into a host cell; raising the level of production of the metabolic compound by inducing expression of csrB; and decreasing the level of production of the metabolic compound by inducing expression of csrA.

BRIEF DESCRIPTION OF THE DRAWINGS

FIG. 1 (SEQ ID NO:1) illustrates the nucleotide sequence of the csrB gene.

FIG. 9 (SEQ ID NO:3) illustrates a nucleotide comparison between csrB of E. coli strain K-12 (upper case) and aepH of Erwinia carotovora (lower case).

DETAILED DESCRIPTION OF THE INVENTION

Figure 2:
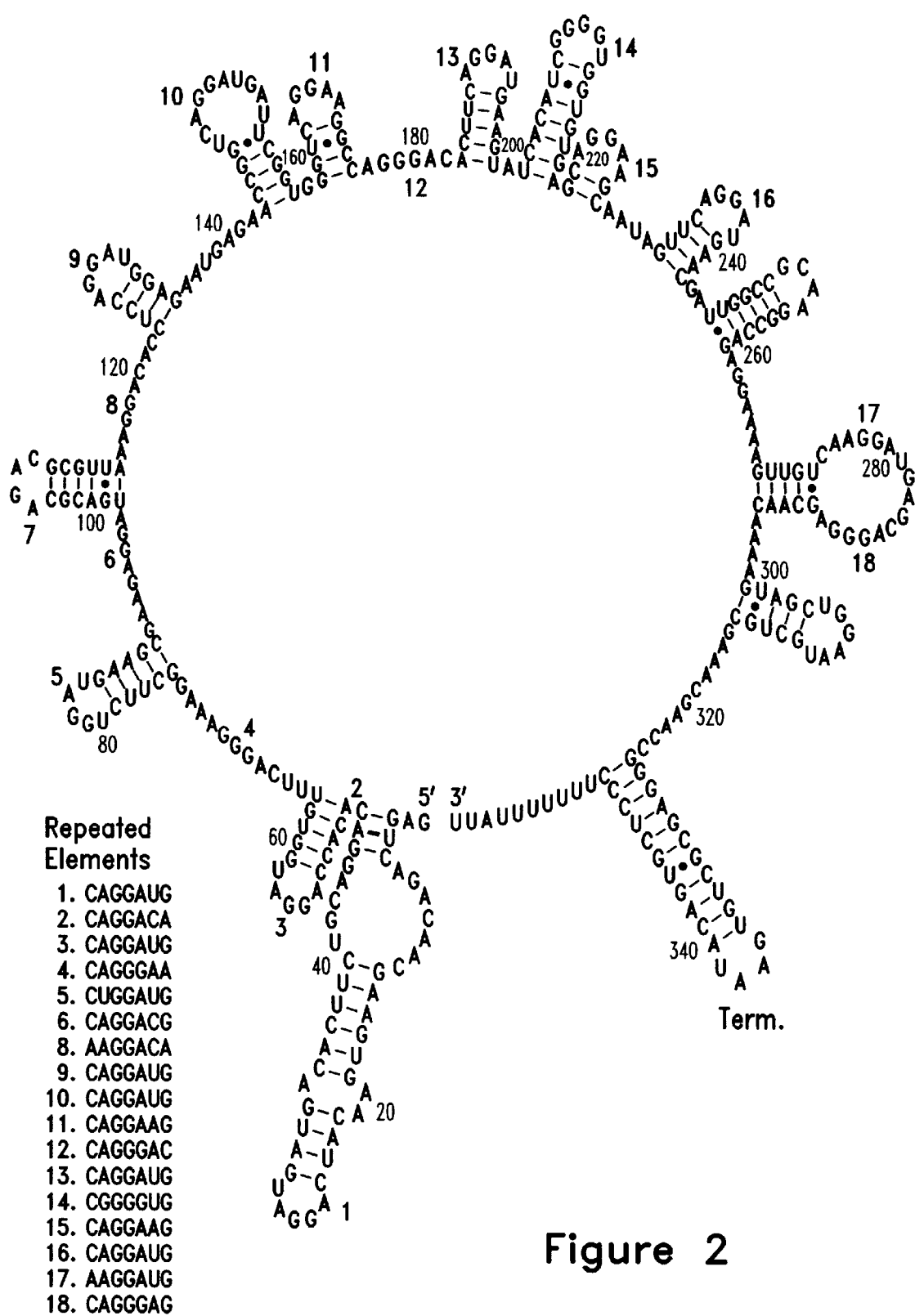
FIG. 2 (SEQ ID NO:2) illustrates the predicted secondary structure of the csrB RNA.

It would be highly advantageous to metabolically engineer bacteria to regulate the flow of precursors through various biochemical pathways to increase production of desired products.

The invention is directed to the csrB gene and the RNA encoded thereby, which binds CsrA and antagonizes its ability to down-regulate expression of metabolic products. The invention is also directed to methods of regulating the expression of a metabolic product by using csrB polynucleotides to modulate the activity of CsrA.

By "csrB RNA" or "csrB gene product" or "csrB transcription product" is meant the RNA encoded by the E. coli csrB gene or RNA substantially homologous or complementary thereto or a derivative or fragment thereof having csrB RNA activity. "csrB RNA activity" is defined as the ability to bind to CsrA and thereby antagonize its activity. A protein may recognize an RNA via the RNA's structure, sequence or both. Encompassed by the definition of "csrB RNA" are variants of csrB in which there have been trivial mutations such as substitutions, deletions, insertions or other modifications of the native csrB RNA which do not prevent csrB from binding CsrA. Trivial mutations include, but are not limited to, mutations which do not prevent or reduce CsrA binding to csrB, such as those which occur outside the regions of csrB bound by CsrA; those within CsrA binding sites that do not affect CsrA binding; those which do not alter the structure of csrB; and double mutations affecting paired members of a stem, such that pairing is retained and binding of CsrA to csrB is not impaired. A csrB polynucleotide of the present invention will have at least one CsrA-binding site, preferably at least about two, more preferably at least about five, even more preferably at least about ten, and most preferably at least about eighteen CsrA binding sites.

The term "substantial homology" or "substantial identity", when referring to polypeptides or polynucleotides, indicates that the sequence of a polypeptide or polynucleotide in question, when properly aligned, exhibits at least about 30% identity with the sequence of an entire naturally occurring polypeptide or polynucleotide or a portion thereof. Polynucleotides of the present invention which are homologous or substantially homologous to, for example, the csrB polynucleotides are usually at least about 70% identity to that shown in FIG. 1 (SEQ ID NO:1), preferably at least 90% identity and most preferably at least about 95% identity and comprise at least one CsrA-binding site or a complement thereof. Any technique known in the art can be used to sequence polynucleotides, including, for example, dideoxynucleotide sequencing [Sanger et al. (1977) Proc. Natl. Acad. Sci. USA 74:5463–5467], or using the Sequenase™ kit (United States Biochemical Corp., Cleveland, Ohio). Homologs of csrB polynucleotides and CsrA polynucleotides and proteins, whether synthetically or recombinantly produced or found in nature, are also encompassed by the scope of the invention, and are herein defined as polynucleotides and polypeptides which are homologous to, respectively, csrB or CsrA polynucleotides and polypeptides or fragments, variants, or complements thereof. Homologous proteins and polynucleotides are generally encoded by homologous genes as described above, and retain significant amino acid residue or nucleotide identity to the CsrA or csrB gene. Such proteins can be expressed by other organisms such as bacteria, yeast and higher order organisms such as mammals. Various methods of determining amino acid residue or nucleotide identity are known in the art. Homologous polypeptides or polynucleotides can be obtained by in vitro synthesis by expressing genes derived from other bacteria or by mutagenizing a gene encoding csrA or csrB. Also included in the definition of "substantially homologous polynucleotides" would be those polynucleotides which, when annealed under conditions known in the art, would remain annealed under moderate wash conditions also known in the art (such as washing in 6×SSPE twice at room temperature and then twice at 37° C.). Wahl et al. (1987) Methods in Enzymology, vol. 152, Academic Press, Inc., San Diego, 1987.

Polypeptide homology is typically measured using sequence analysis software. See, e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, substitutions, and other modifications.

Within the definition of csrB RNA and csrB gene are csrB RNA's and csrB genes containing mutations with increase the ability of csrB to bind CsrA, e.g., by increasing the ability of individual binding sites to bind CsrA or by increasing the number of binding sites. The ability of a csrB mutant to bind CsrA can be tested in vitro using techniques known in the art such as gel retardation, electron microscopy, nuclease studies, and the like. To determine if a csrB mutant antagonizes the activity of CsrA, a quantitative comparison can be made in the output of a chosen CsrA-regulated metabolic product between isogenic bacterial strains producing (1) the wild-type csrB and wild-type CsrA; (2) a mutant csrB and wild-type CsrA; and (3) the wild-type csrB and a mutant CsrA (e.g. csrA::kan$^R$). Strain (3) is a control to demonstrate output levels when such levels are not down-regulated by CsrA. If the mutant csrB in strain (2) is able to antagonize CsrA, the product output of this strain would be higher than that of strain (1). If the mutant csrB is unable to antagonize CsrA, the product output is likely to be lower than that of strains (1) or (3). Most preferably, a mutant csrB would yield product output higher than strain (1).

By "polynucleotide" or "nucleic acid" is meant a single- or double-stranded DNA, genomic DNA, cDNA, RNA, DNA-RNA hybrid, or a polymer comprising purine and pyrimidine bases, or other natural, chemically or biochemically modified or contain non-natural or derivatized nucleotide bases. The backbone of the polynucleotide can comprise sugars and phosphate groups (as typically found in RNA or DNA), or modified or substituted sugar or phosphate groups. Alternatively, the backbone of the polynucleotide can comprise a polymer of synthetic subunits such as phosphoramidates and is thus a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; and Schultz et al. (1996) *Nucleic Acids Res.* 24: 2966–73. In another embodiment, a phosphorothiate linkage can be used in place of a phosphodiester linkage. Braun et al. (1988) *J. Immunol.* 141: 2084–9; Latimer et al. (1995) *Mol. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

A nucleic acid is said to "encode" an RNA or a polypeptide if, in its native state or when manipulated by methods known to those skilled in the art, it can be transcribed and/or translated to produce the RNA, the polypeptide or a fragment thereof. The anti-sense strand of such a nucleic acid is also said to encode the sequence. The csrB and csrA polynucleotides of the present invention comprise those which are naturally-occurring, synthetic or recombinant.

A "recombinant" nucleic acid is one which is chemically synthesized or the product of the artificial manipulation of isolated segments of nucleic acids, e.g., by genetic engineering techniques. Isolated segments within a recombinant nucleic acid can be naturally-occurring sequences.

By "csrB polynucleotide" or "csrB DNA" or "csrB gene" or "csrB RNA" or "csrB polynucleotide" and the like is meant a polynucleotide encoding or comprising csrB RNA or a homolog, fragment, derivative or complement thereof and having csrB RNA activity as described herein. As is known in the art, a DNA can be transcribed by an RNA polymerase to produce RNA, but an RNA can be reverse transcribed by reverse transcriptase to produce a DNA. Thus an DNA can encode a RNA and vice versa.

The invention also encompasses vectors such as single- and double-stranded plasmids or viral vectors comprising RNA, DNA or a mixture or variant thereof, further comprising a csrB polynucleotide, or both csrB and csrA genes, or a pair of vectors, one comprising the csrA gene, the other comprising the csrB gene. A wide variety of suitable expression systems are known in the art and are selected based on the host cells used, inducibility of expression desired and ease of use. The non-transcribed portions of csrB gene and the non-coding portions of the csrA gene can be modified as known in the art. For example, the native promoters can be deleted, substituted or supplemented with other promoters known in the art; transcriptional enhancers, inducible promoters or other transcriptional control elements can be added, as can be replication origins and replication initiator proteins, autonomously replicating sequence (ARS), marker genes (e.g. antibiotic resistance markers), sequences for chromosomal integration (e.g., viral integration sites or sequences homologous to chromosomal sequences), restriction sites, multiple cloning sites, ribosome-binding sites, RNA splice sites, polyadenylation sites, transcriptional terminator sequences, mRNA stabilizing sequences, and other elements commonly found on plasmids and other vectors known in the art. Secretion signals from secreted polypeptides can also be included to allow the polypeptide to cross and/or lodge in cell membranes or be secreted from the cell. Such vectors can be prepared by means of standard recombinant techniques discussed, for example, in Sambrook et al. (1989) *Molecular Cloning: A Laboratory Manual*, 2d. edition, Cold Spring Harbor Press, Cold Spring Harbor, N.Y., and Ausubel et al. (eds.), (1987) *Current Protocols in Molecular Biology*, Greene Publishing Associates, Brooklyn, N.Y. Many useful vectors are known in the art and can be obtained from vendors including, but not limited to, Stratagene, New England Biolabs, Promega Biotech.

An appropriate promoter and other necessary vector sequences is selected so as to be functional in the chosen host. While prokaryotic host cells are preferred, mammalian or other eukaryotic host cells, including, but not limited to, yeast, filamentous fungi, plant, insect, amphibian or avian species, can also be useful for production of the proteins of the present invention. See, *Tissue Culture*, Kruse et al., eds., Academic Press (1973). Examples of workable combinations of cell lines and expression vectors are described in Sambrook et al. (1989) or Ausubel et al. (1987); see also, e.g., Metzger et al. (1988) *Nature* 334:31–36. Examples of commonly used mammalian host cell lines are VERO and HeLa cells, Chinese hamster ovary (CHO) cells, and WI38, BHK, and COS cell lines, or others as appropriate, e.g., to provide higher expression, desirable glycosylation patterns, etc.

By "bacterial host cell" or "bacteria" or "bacterium" is meant various micro-organism(s) containing at least one chromosome but lacking a discrete nuclear membrane. Representatives include *E. coli*, Bacillus, Salmonella, Pseudomonas, Staphylococcus and other eubacteria, archaebacteria, chiamydia and rickettsia and related organisms, and the like, and may be spherical, rod-like, straight, curved, spiral, filamentous or other shapes.

Vectors suitable for use with various cells can comprise promoters which can, when appropriate, include those naturally associated with csrA genes. Promoters can be operably linked to a csrB- or csrA-encoding polynucleotide.

A nucleic acid sequence is "operably linked" when it is placed into a functional relationship with another nucleic acid sequence. For instance, a promoter is operably linked to a coding sequence if the promoter affects the transcription or expression of the gene. Generally, operably linked means that the DNA sequences being linked are contiguous and, where necessary to join two protein coding regions, contiguous and in reading frame.

Promoters can be inducible or repressible by factors which respond biochemically to changes in temperature, osmolarity, carbon source, sugars, etc., as is known in the art. Promoters including, but not limited to, the trp, lac and phage promoters, tRNA promoters and glycolytic enzyme promoters can be used in prokaryotic hosts. Useful yeast promoters include, but are not limited to, the promoter regions for metallothionein, 3-phosphoglycerate kinase or other glycolytic enzymes such as enolase or glyceraldehyde-3-phosphate dehydrogenase, enzymes responsible for maltose and galactose utilization. Suitable vectors and promoters for use in yeast expression are further described in Hitzeman et al. EP 73,657A. Appropriate foreign mammalian promoters include, but are not limited to, the early and late promoters from SV40 (Fiers et al. (1978) *Nature* 273:113) and promoters derived from murine Moloney leukemia virus, mouse mammary tumor virus, avian sarcoma viruses, adenovirus II, bovine papilloma virus or polyoma. In addition, the construct can be joined to an amplifiable gene (e.g., DHFR) so that multiple copies of the construct can be made. For appropriate enhancer and other expression control sequences suitable for vectors, see also *Enhancers and Eukaryotic Gene Expression*, Cold Spring Harbor Press: N.Y., 1983.

While expression vectors are preferably autonomously replicating, they can also be inserted into the genome of the host cell by methods known in the art. Expression and cloning vectors preferably contain a selectable marker which is a gene encoding a protein necessary under at least one control for the survival or growth of a host cell transformed with the vector. The presence of this gene ensures the growth of only those host cells which express the inserts. Typical selection genes are known in the art and include, but are not limited to, those which encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker depends on the host cell, as appropriate markers for different hosts are well known.

As one of skill in the art will understand, the choice in construction and arrangement of markers, promoters, origins of replication, csrB and csrA genes, etc. on various vectors of the present invention will be dictated by the desired level and timing of expression of csrB RNA and/or CsrA, with the ultimate goal of regulating the production of metabolic compounds in the host cell.

As stated above, the present invention encompasses vectors encoding csrB RNA (or homologs, fragments, derivatives and complements thereof) or both csrB RNA and CsrA (or homologs, fragments, derivatives and complements thereof). The invention also encompasses pairs of vectors, one vector comprising the csrB gene (or a homolog, fragment, derivative or complement thereof), the other vector comprising the csrA gene (or a homolog, fragment, derivative or complement thereof).

A vector comprising both csrB and csrA genes can be useful, for example, for controlling the timing and level of expression of a desired CsrA-regulated metabolic product. For example, on such a vector, expression of csrB can be controlled by one inducible promoter (e.g. a heat-inducible promoter), while expression of csrA can be controlled by another type of inducible promoter (e.g. a cold-inducible promoter, as described, for example, in Vasina et al. (1996) *Appl. Environ. Microbiol.* 62: 1444–7). When high levels of the metabolic product are desired, the cells can be grown at a high temperature, such that csrB RNA is overproduced, which then binds to and antagonizes CsrA, yielding high levels of production. If it is desired that production levels be lowered (e.g. if overproduction of the product is toxic, or if cells are being manipulated during at time at which overproduction would be inconvenient), the cells might be switched to and grown at a lower temperature, whereat CsrA would be overproduced, leading to lower production of the desired product.

Inside a bacterial cell, multiple CsrAs can be noncovalently bound to a single csrB RNA, forming a large multisubunit ribonucleoprotein complex. Experimental evidence supports the model that csrB RNA antagonizing the effect of CsrA by competing with cellular mRNA's for binding to CsrA.

By "CsrA" or "CsrA protein" or "CsrA polypeptide" is meant a polypeptide encoded by the *E. coli* csrA gene or a polypeptide substantially homologous thereto and having CsrA activity. Encompassed by the CsrAs are variants of CsrA in which there have been trivial substitutions, deletions, insertions or other modifications of the native CsrA polypeptide which substantially retain CsrA characteristics, particularly silent or conservative substitutions. Silent nucleotide substitutions are changes of one or more nucleotides which do not change any amino acid of CsrA. Conservative substitutions include substitutions within the following groups: glycine, alanine; valine, isoleucine, leucine; aspartic acid, glutamic acid; asparagine, glutamine; serine, threonine; lysine, arginine; and phenylalanine, tyrosine. Such conservative substitutions are not expected to interfere with CsrA biochemical activity, particularly when they occur in structural regions (e.g., alpha helices or beta pleated sheets) of the polypeptide, which can be predicted by standard computer analysis of the amino acid sequence of *E. coli* CsrA. Also encompassed by the claimed CsrA polypeptides are polypeptides encoded by polynucleotides which are substantially homologous to a polynucleotide encoding CsrA [as defined, for example, in Romeo et al. (1993a); Romeo et al. (1993b); Liu et al. (1995); Sabnis et al. (1995); Yang et al. (1996) *J. Bacteriol.* 178:1012–1017, or any other reference cited herein].

By "csrA" or "csrA gene" is meant the gene encoding the protein CsrA as described above, or a homolog, variant, fragment or complement of such gene. The DNA sequence is presented in references cited herein, however, it is to be understood that modifications can be made to the sequence without impairing its ability to encode CsrA. Due to degeneracy in the genetic code there is some degree of flexibility in the third base of each codon and some amino acid residues are encoded by several different codons. Each possible codon could be used in the gene to encode the protein. While this may appear to present innumerable choices, in practice, each host has a particular preferred codon usage, so that genes can be tailored for optimal translation in the host in which they are expressed. Thus, synthetic genes that encode CsrA are included in this invention.

By "csrA RNA" or "csrA DNA" or "csrA polynucleotide" or "csrA nucleic acid" is meant a polynucleotide encoding CsrA or a homolog, derivative, complement or fragment thereof. Nucleic acids encoding the CsrA polypeptides of the present invention include not only native or wild-type csrA sequences but also any sequence capable of encoding a CsrA polypeptide, which can be synthesized by making use of the redundancy in the genetic code. Various codon substitutions can be introduced, e.g., silent or conservative changes as discussed above.

Techniques for nucleic acid manipulation are described generally, for example, in Sambrook et al., 1989 and Ausubel et al., 1987. Reagents useful in applying such techniques, such as restriction enzymes and the like, are widely known in the art and commercially available from vendors including, but not limited to, New England BioLabs, Boehringer Mannheim, Amersham, Promega Biotech, U. S. Biochemicals, New England Nuclear, and a number of other sources.

Nucleic acid probes and primers based on csrA or csrB sequences can be prepared by standard techniques. Such a probe or primer comprises an isolated nucleic acid. In the case of probes, the nucleic acid further comprises a label (e.g., a radionuclide such as $^{32}$P ATP or $^{35}$S) or a reporter molecule (e.g., a ligand such as biotin or an enzyme such as horseradish peroxidase). The [$^{32}$P]-ATP, [$^{35}$S]-dATP and [$^{35}$S] methionine can be purchased, for example, from DuPont NEN (Wilmington, Del.). Probes can be used to identify the presence of a hybridizing nucleic acid sequence, e.g., a csrA mRNA or csrB RNA in a sample or a cDNA or genomic clone in a library. Primers can be used, for example, for amplification of nucleic acid sequences, e.g., by the polymerase chain reaction (PCR). See, e.g., *PCR Protocols: A Guide to Methods and Applications,* Innis et al., eds., Academic Press: San Diego (1990). The preparation and use of probes and primers is described, e.g., in Sambrook et al. (1989) or Ausubel et al. (1987). The genes of homologs of csrB and csrA in other species can be obtained by generating cDNA from RNA from such species using any technique known in the art, such as using Riboclone cDNA Synthesis Systems AMV RT (Promega, Madison, Wis.), then probing such cDNA with radiolabeled primers containing various portions (e.g. 30 or 40 bases long) of the sequences of csrA and csrB disclosed herein and in references cited herein. To obtain homologs of CsrA, degenerate primers can encode the amino acid sequence of the disclosed *E. coli* csrA but differ in codon usage from the sequences disclosed.

Antisense nucleic acids capable of specifically binding to csrA sequences are also useful for interfering with csrA gene expression. See, e.g., EPO publication 431523A2.

Antisense nucleic acids capable of specifically binding to csrB can be used in the present invention to modulate the ability of csrB to bind CsrA. For example, it may be desirable that high production of a metabolic product be achieved and then later repressed. In this case, for example, first high levels of csrB can be expressed to repress CsrA activity, thereby causing high product production. Then, to limit product production, an antisense nucleic acid can be expressed (e.g. via an inducible promoter), which then binds and titrates csrB, thus allowing CsrA to suppress product production.

The nucleic acids of the present invention (whether sense or anti-sense, and whether encoding CsrA, csrB or a homolog, variant, fragment or complement thereof) can be produced in large amounts by replication of a suitable recombinant vector comprising csrA sequences in a compatible host cell. Alternatively, these nucleic acids can be chemically synthesized, e.g., by any method known in the art, including, but not limited to, the phosphoramidite method described by Beaucage et al. (1981) *Tetra. Letts.* 22:1859–1862 and the triester method according to Matteucci et al. (1981) *J. Am. Chem. Soc.* 103:3185, preferably using commercial automated synthesizers. The purification of nucleic acids produced by the methods of the present invention can be achieved by any method known in the art including, but not limited to, those described, e.g., in Sambrook et al. (1989) or Ausubel et al. (1987). Numerous commercial kits are available for DNA purification including Qiagen plasmid mini DNA cartridges (Chatsworth, Calif.).

The nucleic acids of the present invention can be introduced into host cells by any method known in the art, which vary depending on the type of cellular host, including, but not limited to, electroporation; transfection employing calcium chloride, rubidium chloride calcium phosphate, DEAE-dextran, or other substances; microprojectile bombardment; P1 transduction; use of suicide vectors; lipofection; infection (where the vector is an infectious agent, such as a retroviral genome); and other methods. See generally, Sambrook et al. (1989) and Ausubel et al. (1987). The cells into which these nucleic acids have been introduced also include the progeny of such cells.

This invention also encompasses compositions comprising a csrB polynucleotide in combination with one or more CsrA or fragments, homologs or derivatives thereof. More preferably, the ratio of CsrA to csrB polynucleotides is greater than 5:1, preferably less than 50:1, most preferably around 18:1. However, this invention encompasses any ratio of CsrA protein to csrB polynucleotide, including by not limited to, for example, the ratios of 1:1, greater than 1:1, greater than 2:1, greater than 5:1, greater than 10:1, greater than 100:1, greater than 1000:1, greater than 10,000:1, greater than 100,000:1, or greater than 1,000,000:1. The invention also encompasses ratios of CsrA to csrB polynucleotide of 1:1, less than 1:1, less than 1:2, less than 1:5, less than 1:10, less than 1:100, less than 1:1000, less than 1:10,000; less than 1:100,000; or less than 1,000,000. The combination of csrB polynucleotide and CsrA can be substantially pure of other components. Alternatively, other components such as carbon sources of metabolism-regulating factors can be added to the combination. The combinations of the invention can comprise full-length CsrA or biologically active fragments or derivatives thereof which retain the ability to bind csrB polynucteotide, or full-length csrB or biologically active fragments or derivatives thereof which retain the ability to bind CsrA. The combinations of csrB polynucleotides and CsrA of the present invention can comprise csrB and CsrA bound to each other, unbound (free), in flux between bound and unbound states, or can comprise a mixture of bound and unbound molecules. The combinations of nucleotides and polypeptides of the present invention can be coupled to a solid phase support, e.g., nitrocellulose, nylon, column packing materials (e.g., Sepharose beads), magnetic beads, glass wool, cells, or other substrates.

The present invention also provides for combinations of a csrB polynucleotide (or fragments or derivatives thereof) with CsrA or fragments thereof which have been modified, by methods including, but not limited to, in vivo or in vitro chemical and biochemical modifications or by the incorporation of unusual amino acids. Such modifications include, for example, acetylation, carboxylation, phosphorylation, glycosylation, ubiquitination, and labeling, e.g., with radionuclides, or various enzymatic modifications. There are a variety of standard methods for labeling polypeptides and labels useful for such purposes, including radioactive isotopes such as $^{32}$P, ligands which bind to labeled antiligands (e.g., antibodies) or antiligands which bind to labeled ligands, fluorophores, chemiluminescent agents, and enzymes. See, e.g., Sambrook, et al. (1989); or Ausubel et al. (1987).

The present invention also provides for combinations of csrB polynucleotides with fusion polypeptides comprising CsrA polypeptides and fragments thereof. Such fusions can be between two or more CsrA sequences or between the sequences of CsrA and a related or unrelated polypeptide. Such fusion polypeptides can exhibit a combination of properties or activities of the derivative proteins. For immunological purposes, tandemly repeated polypeptide segments can be used as immunogens, thereby producing highly antigenic proteins. Alternatively, such polypeptides can serve as highly efficient competitors for binding. Fusion partners include immunoglobulins, bacterial β-galactosidase, trpE, protein A, β-lactamase, alpha amylase, alcohol dehydrogenase and yeast alpha mating factor. See, e.g., Godowski et al. (1988) *Science* 241:812–816. Where desired, a signal peptide or leader sequence can be added by recombinant DNA techniques, e.g., to the amino terminus of CsrA, to direct the polypeptide through the membrane of a cell.

A polypeptide "fragment," "portion," or "segment" is a stretch of amino acid residues of at least about 7 to 17 amino acids (or the minimum size retaining an antigenic determinant of CsrA and capable of raising CsrA-specific antibodies). A CsrA of the present invention can, alternatively, comprise a portion of at least 20 amino acids of the CsrA sequence, at least 30 amino acids of the CsrA sequence, at least 40 amino acids of the CsrA sequence, at least 50 amino acids of the CsrA sequence, or all or substantially all of the CsrA sequence. In addition, the invention encompasses the combination of csrB polynucleotides (or fragments or derivatives thereof) with CsrA polypeptides which comprise a portion of the CsrA sequence of the lengths described in this paragraph, which further comprise additional amino acid sequences on the ends or in the middle of CsrA sequences. The additional amino acid sequences can, for example, comprise another protein or a functional domain thereof, such as signal peptides, membrane-binding moieties, etc.

A polynucleotide fragment of csrB polynucleotide of the present invention, either isolated or in combination with CsrA, can comprise a polymer of at least six bases or basepairs, preferably comprising a sequence capable of being bound by CsrA. A fragment of the present invention can comprise at least six bases or basepairs, at least 10 bases or basepairs, at least twenty bases or basepairs, at least forty bases or base pairs, at least fifty bases or basepairs, at least one hundred bases or basepairs, at least one hundred fifty bases or basepairs, at least two hundred bases or basepairs, at least two hundred fifty bases or basepairs, at least three hundred bases or basepairs of the csrB gene sequence, or can comprise all or substantially all of the csrB sequence. In addition, the invention encompasses polynucleotides which comprise a portion of the csrB sequence of the lengths described in this paragraph, which further comprise additional sequences on the 5' or 3' end or inserted into the csrB sequence. These additional sequences can, for example, encode a coding region of a gene or a functional domain thereof or a promoter. These polynucleotides can be in combination with CsrA polypeptides or fragments or derivatives thereof.

The terms "isolated," "pure," "substantially pure," and "substantially homogenous" are used interchangeably to describe a polypeptide, or polynucleotide which has been separated from components which naturally accompany it. A monomeric protein or a polynucleotide is substantially pure when at least about 60 to 75% of a sample exhibits a single polypeptide or polynucleotide sequence. A substantially pure protein or polynucleotide typically comprises about 60 to 90% by weight of a protein or polynucleotide sample, more usually about 95%, and preferably will be over about 99% pure.

Protein or polynucleotide purity or homogeneity may be indicated by a number of means, such as polyacrylamide gel electrophoresis of a sample, followed by visualizing a single band upon staining the gel. For certain purposes higher resolution can be provided by using high performance liquid chromatography (HPLC) or other means well known in the art for purification.

A csrB RNA or CsrA is "isolated" when it is substantially separated from the contaminants which accompany it in its natural state. Thus, a polypeptide which is chemically synthesized or expressed as a recombinant protein, i.e., an expression product of an isolated and manipulated genetic sequence, is considered isolated. A recombinant polypeptide is considered "isolated" even if expressed in a homologous cell type.

A CsrA polypeptide can be purified from cells in which it is produced by any of the purification methods known in the art. For example, such polypeptides can be purified by immunoaffinity chromatography employing, e.g., the antibodies provided by the present invention. Various methods of protein purification include, but are not limited to, those described in *Guide to Protein Purification*, ed. Deutscher, vol. 182 of *Methods in Enzymology* (Academic Press, Inc., San Diego, 1990) and Scopes, *Protein Purification: Principles and Practice* (Springer-Verlag, New York, 1982).

Polypeptide fragments of CsrA are first obtained by digestion with enzymes such as trypsin, clostripain, or Staphylococcus protease or with chemical agents such as cyanogen bromide, O-iodosobenzoate, hydroxylamine or 2-nitro-5-thiocyanobenzoate. Peptide fragments can be separated by reversed-phase HPLC and analyzed by gas-phase sequencing. Peptide fragments are used in order to determine the partial amino acid sequence of a polypeptide by methods known in the art including but not limited to, Edman degradation.

Another embodiment of the present invention is a method of altering metabolic pathways controlled by csrA. Such pathways include but are not limited to glycogen biosynthesis and gluconeogenesis. Such methods are useful for directly increasing or decreasing expression of genes that are directly under csrA control and for indirectly enhancing production of products via pathways that are not under csrA control. Such products include, but are not limited to, antibiotics, acetic acid, amino acids, organic acids, alcohols, and a wide variety of other industrially important compounds produced in bacterial fermentation systems. The suitable methods of altering the expression of csrA are known in the art and include, but are not limited to, the methods described herein.

The present invention also provides polyclonal and/or monoclonal antibodies capable of specifically binding to a csrB polynucleotide or a complex of a csrB polynucleotide and at least one CsrA polypeptide or homolog, fragment, complement or derivative thereof. Antibodies to such complexes can be distinct from antibodies capable of binding specifically to free (unbound) CsrA, as the act of binding to csrB can alter the CsrA structure and thereby expose CsrA epitopes which are otherwise buried. Antibodies can also be produced which bind specifically to a csrB polynucleotide, such as a csrB RNA or fragments thereof, and may be produced as described in, for example, Thiry (1994) *Chromosoma* 103: 268–76; Thiry (1993) *Eur. J. Cell. Biol.* 62: 259–69; Reines (1991) *J. Biol. Chem.* 266: 10510–7; Putterman et al. (1996) *J. Clin. Invest.* 97: 2251–9; Fournie (1996) *Clin. Exp. Immunol.* 104: 236–40. This invention also encompasses antibodies which bind specifically to epitopes of csrB polynucleotides which are not exposed in a csrB RNA-CsrA complex. Antibodies capable of binding to csrB polynucleotides or complexes of CsrA and csrB polynucleotide can be useful in detecting CsrA, in titrating CsrA to further prevent it from suppressing the production of metabolic products, for quantifying CsrA, for purifying CsrA or complexes of a csrB polynucleotide and CsrA, or for other uses.

For production of polyclonal antibodies, an appropriate host animal is selected, typically a mouse or rabbit. The substantially purified antigen, whether the whole CsrA polypeptide, a fragment, derivative, or homolog thereof, or a CsrA polypeptide coupled or fused to another polypeptide, or any of these in combination with a csrB polynucleotide or homolog, derivative, complement or fragment thereof, is presented to the immune system of the host by methods appropriate for the host, commonly by injection into the footpads, intramuscularly, intraperitoneally, or intradernally. Peptide fragments suitable for raising antibodies can be prepared by chemical synthesis, and are commonly coupled to a carrier molecule (e.g., keyhole limpet hemocyanin) and injected into a host over a period of time suitable for the production of antibodies. The sera are tested for immunoreactivity to the CsrA protein or fragment. Monoclonal antibodies can be made by injecting the host with the protein polypeptides, fusion proteins or fragments thereof and following methods known in the art for production of such antibodies. See Harlow et al. (1988) *Antibodies: A Laboratory Manual,* CSH Laboratories.

An immunological response is usually assayed with an immunoassay, a variety of which are provided, e.g., in Harlow et al. (1988); or Goding (1986) *Monoclonal Antibodies: Principles and Practice,* 2d ed., Academic Press, New York, although any method known in the art can be used.

Monoclonal antibodies with affinities of $10^8$ M$^{-1}$, preferably $10^9$ to $10^{10}$, or stronger are made by standard procedures as described, e.g., in Harlow et al. (1988) or Goding (1986). Briefly, appropriate animals are immunized with the antigen by a standard protocol. After the appropriate period of time, the spleens of such animals are excised and individual spleen cells fused to immortalized myeloma cells. Thereafter the cells are clonally separated and the supernatants of each clone are tested for their production of an appropriate antibody specific for the desired region of the antigen.

Other suitable techniques of antibody production include, but are not limited to, in vitro exposure of lymphocytes to the antigenic polypeptides or selection of libraries of antibodies in phage or similar vectors. Huse et al. (1989) *Science* 246:1275–1281.

Frequently, the polypeptides and antibodies are labeled, either covalently or noncovalently, with a substance which provides for a detectable signal. A wide variety of labels and conjugation techniques are known. Suitable labels include, but are not limited to, radionuclides, enzymes, substrates, cofactors, inhibitors, fluorescent agents, chemiluminescent agents, magnetic particles. Patents, teaching the use of such labels include, but are not limited to, U.S. Pat. Nos. 3,817, 837; 3,850,752; 3,939,350; 3,996,345; 4,277,437; 4,275, 149; and 4,366,241.: Also, recombinant immunoglobulins can be produced by any method known in the art. See Cabilly, U.S. Pat. No. 4,816,567.

By "metabolic product" is meant any sugar, amino acid. protein, alcohol, acid, organic compound, non-organic compound, or derivative or chemically modified version of any of the above which is produced as a result of a biosynthetic pathway.

MODES FOR CARRYING OUT THE INVENTION

Csr is a regulatory system which was originally identified via a mutation which inactivates a small RNA binding protein, CsrA, which is the central factor of this system. Romeo et al. (1993a). CsrA is a negative regulator of certain processes associated with the early stationary phase of growth, including glycogen synthesis and catabolism [Romeo et al. (1993a); Yanget al. (1996)] and gluconeogenesis [Romeo et al. (1993a); Sabnis et al. (1995)] in the bacterium *E. coli,* and a CsrA homolog mediates the expression of several extracellular virulence factors in the bacterium *Erwinia carotovora.* Chatterjee et al. (1995) *Appl. Environ. Microbiol.* 61:1959–1967; and Cui et al. (1995). CsrA also modulates the glycolytic pathway in *E. coli* [Sabnis et al. (1995)], affects cell surface properties [Romeo et al. (1993a)], and has been proposed to directly or indirectly affect DNA gyrase activity. Muryama et al. (1996) *J. Mol. Biol.* 256:483–502. CsrA is related to a diverse subset of RNA-binding proteins known as KH proteins and it regulates glycogen biosynthesis pathway by binding to and facilitating decay of the glgCAP message. Liu et al. (1995).

Purified recombinant CsrA binds to a circa 350 nucleotide RNA in a large globular multisubunit complex. The fact that 14 different cDNA clones generated from this RNA all originated from a single genetic locus in *E. coli* showed that it was not a collection of various CsrA-regulated messages bound to CsrA in an intermediate state of turnover, but represented a single gene product, designated csrB.

RNA was purified from the CsrA-csrB complex by extraction once with phenol:chloroform (1:1), once with chloroform, and precipitation with ethanol. RNA was quantified by absorbance at 260 nm or by orcinol assay. Schmidt et al. (1945) *J. Biol. Chem.* 181:83–89. For molecular mass estimation, purified RNA was electrophoresed on 1.2% agarose gels containing 2.2 M formaldehyde. Sambrook et al. (1989).

cDNA was prepared by treating csrB RNA (5 μg) with polyA polymerase (4 units) in a reaction containing 250 μM ATP, 40 mM Tris HCl pH 8.0, 10 mM MgCl$_2$, 2.5 mM MnCl$_2$, 250 mM NaCl, 1 mM DTT, followed by cDNA synthesis using the Riboclone cDNA Synthesis Systems AMV RT (Promega, Madison, Wis.) according to the manufacturer's specifications. cDNA was made blunt-ended using T4 DNA polymerase and was cloned into the SmaI site of vector pUC19 [Yanish-Perron et al. (1985) *Gene* 33:103–119] using *E. coli* strain DH5α for transformation. Approximately 200 clones were saved, 14 of which were at least partially sequenced and mapped on the *E. coli* genome using database searches.

Extensive endonucleolytic degradation of the csrB and repurification of the RNA-free CsrA did not inactivate CsrA, but rather generated a preparation which was more active in down-regulating gene expression in S-30 transcription-translation reactions. These results showed that csrB RNA is not required for CsrA activity; thus the CsrA-csrB complex is not a ribozyme. Furthermore, csrB lacks a significant open reading frame, and does not appear to be a mRNA. Finally, overexpression of csrB in E. coli strains wild type for csrA caused an increase in intracellular glycogen levels, which are under strong negative control of CsrA, while a strain defective in csrA showed no effect of increased csrB. csrB is thus a second regulatory component of the Csr system and provides a novel RNA molecule function, sequestration and inhibition or antagonism of an mRNA decay factor.

Further evidence of the regulatory function of csrB is derived from previous studies of the csrB homolog of another species of the Enterobacteriaceae, the plant pathogen *Erwinia carotovora*. Murata et al. (1994) *Appl. Environ. Microbiol.* 60:3150–3159. The csrB homolog of *E. carotovora*, aepH, antagonizes the highly-conserved csrA homolog of this species, rsmA. Cui et al. (1995). The aepH region positively regulates several secreted virulence proteins which are repressed by rsmA. The mechanism for the positive effects of aepH on these virulence proteins has not been shown, except that transcription levels of regulated genes were affected. Murata et al. (1994). Taken in context with the studies reported here for the *E. coli* csrB RNA, the small open reading frame previously noted in the aepH region of the *E. carotovora* genome probably does not encode the regulatory factor responsible for these effects. Furthermore, (i) there is no evidence the AepH protein is actually synthesized; (ii) the aepH open reading frame is not conserved in *E. coli*; (iii) the highly-repeated sequence elements noted for *E. coli* csrB RNA are conserved in *E. carotovora*; (iv) transposition mutations and deletions significantly upstream from the aepH reading frame, but within or slightly upstream from the repeated elements in *E. carotovora* inactivated the regulatory function of this region, and indicated that the repeated elements are functional. Murata et al. (1994).

Figure 7:
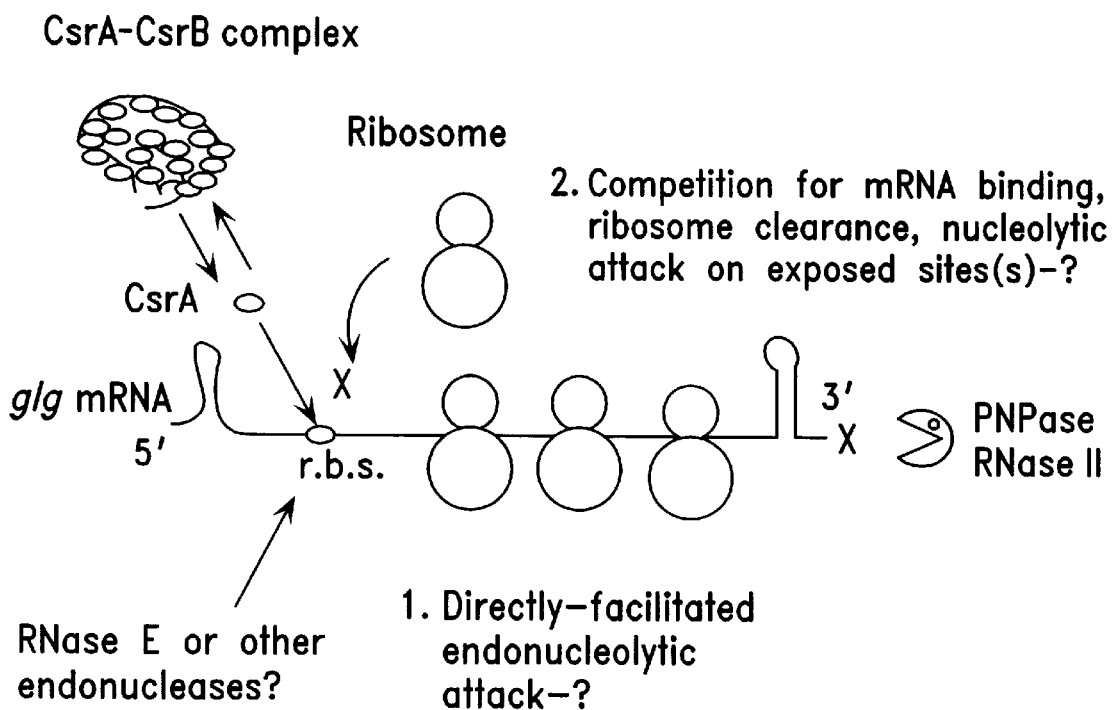
FIG. 7 illustrates the regulatory interactions in the Csr system, including a proposed model for posttranscriptional regulation of gene expression by CsrA and csrB RNA.
Figure 8:
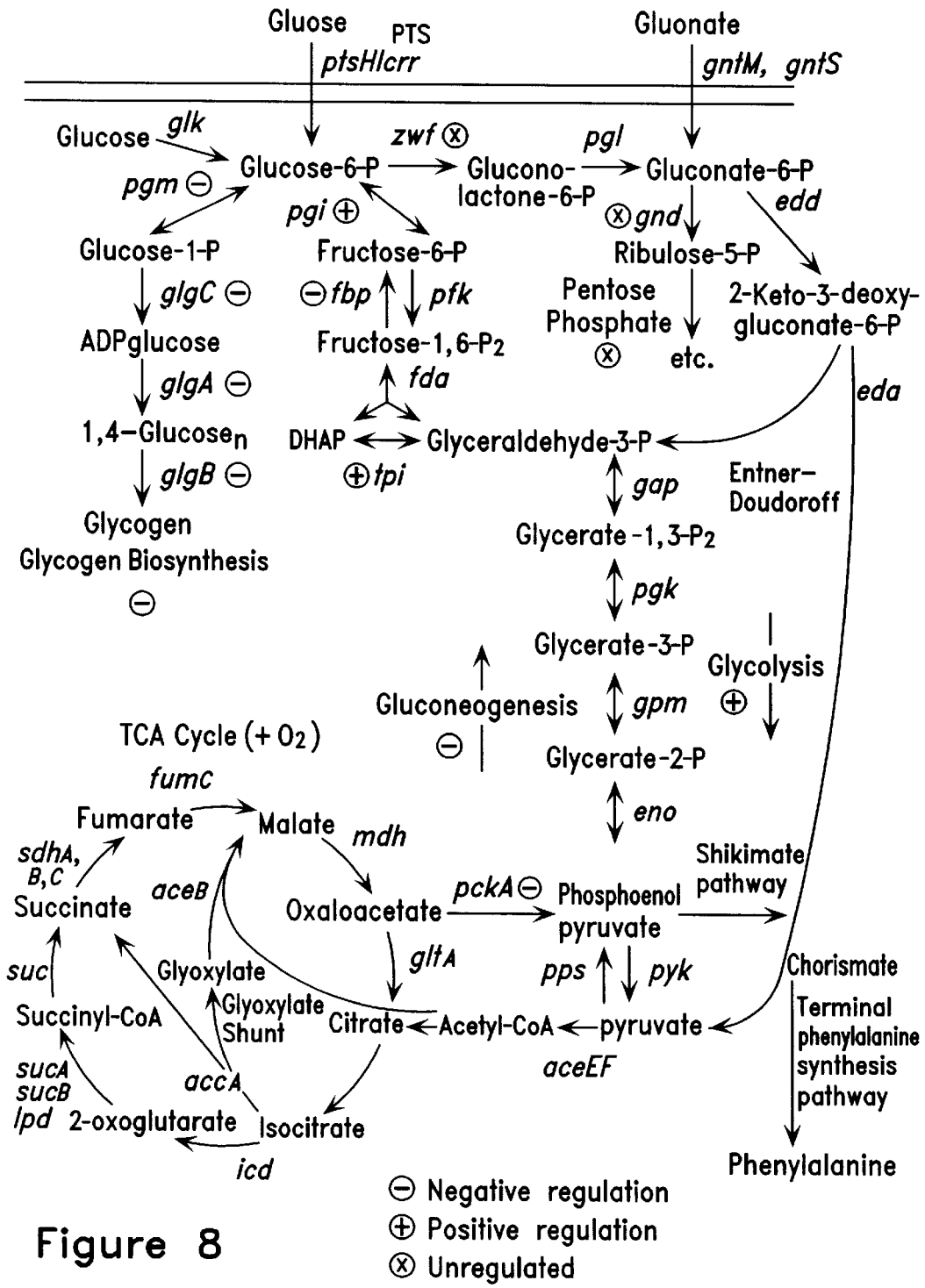
FIG. 8 illustrates the regulatory effects of CsrA on intermediary carbon metabolism.

The Csr systems of *E. coli* and *E. carotovora* thus apparently include but are not necessarily limited to, a regulatory RNA transcript, csrB, which binds to and antagonizes the activity of an RNA-binding protein, CsrA or its homolog RsmA. CsrA functions by modulating mRNA stability. A model depicting these interactions within Csr is shown in FIG. 7. Factors which affect csrB levels in the cell should determine the activity of CsrA. Furthermore, turnover of csrB RNA presents an effective means to rapidly increase the active concentration of CsrA in the cell and halt the expression of CsrA-inhibited genes by causing their mRNA's to be degraded. Thus, Csr can be used as a means of modulating gene expression in biotechnology applications, independently of or in addition to existing transcriptional control mechanisms.

While being bound by any specific explanation for the mechanism by which csrB antagonizes CsrA activity, FIG. 7 illustrates a proposed model for posttranscriptional regulation of gene expression by CsrA and csrB RNA. CsrA activity is hypothesized to be controlled through an equilibrium which exists between the free and csrB-bound protein. In this model, accumulation of csrB in the cell would tend to activate CsrA-repressed genes, while turnover of csrB RNA would release CsrA and inhibit CsrA-repressed genes, such as glgC. Alternative mechanisms are also indicated by which CsrA binding to mRNA such as glgCAP may facilitate its decay. Liu et al. (1995). 1. The CsrA-mRNA complex may be a direct substrate for endonuclease activity or CsrA binding may alter mRNA structure, making it accessible to endonucleolytic attack. 2. CsrA binding may inhibit ribosome loading and translation, followed by clearance of translating ribosomes and exposure of mRNA to turnover. A combination of these mechanisms may also occur.

The binding of 18 CsrA subunits to csrB RNA to form a ribonucleoprotein complex and that 18 imperfect repeated elements are localized to predicted single stranded regions of csrB RNA show that the sequence CAGGA(U,A,C)G serves as a recognition element for CsrA. The complement of this sequence is C(G,U,A)UCCUG or, in the corresponding DNA, C(G,T,A)TCCTG. This sequence is related to the Shine-Dalgarno (SD) sequence [Shine et al. (1974) *Proc. Natl. Acad. Sci. USA* 71:1342–1346]. The SD sequence is involved in binding of the ribosome to mRNA. The cis-acting region for the regulation of glgC expression by CsrA approximates the ribosome binding site. Liu et al. (1995).

No other bacterial RNAs are currently known to function in the same capacity as csrB, although the number and variety of transcripts with trans-acting regulatory functions is growing rapidly. Examples include several antisense RNA's, RNA III of *S. aureus*, a global regulator of virulence factors and which can affect gene transcription as well as translation [Morfeldt et al. (1995) *EMBO J.* 14:4569–4577], and the small *E. coli* transcript DsrA, which regulates the transcription of rcsA (a regulatory gene for capsule biosynthesis). Sledjeski et al. (1995) *Proc. Natl. Acad. Sci. USA* 92:2003–2007.

The invention is better understood by reference to the following examples, which merely illustrate but not limit the best mode now known for practicing the invention.

EXAMPLE 1

Expression and Purification of Recombinant CsrA-H6

The present invention encompasses combinations of csrB RNA (or homologs, derivatives, complements and fragments thereof) and CsrA polypeptides (or homologs, derivatives and fragments thereof). CsrA can be expressed by any of the expression and purification techniques known in the art, or by the techniques described herein, or a suitable modification thereof.

Based upon previous experiments which showed that the carboxy-terminus of CsrA could be modified without destroying its in vivo biological activity [Romeo et al. (1 993a)], a plasmid, pCSRH6-19, was constructed to allow the expression and over-expression of recombinant CsrA containing 6 histidine residues at the carboxy-terminus, permitting protein purification via metal-binding affinity chromatography. Janknecht et al. (1991) *Proc. Natl. Acad. Sci. USA* 88:8972–8976.

To construct pCSRH6-19, a PCR product containing the csrA coding region and 6 in-frame histidine codons followed by a termination codon was prepared using HindIII-treated CsrA-H6-overproducing plasmid pCSR10 [csrA cloned into pUC19, Romeo et al. (1993a)] and the oligonucleotide primers ATGCTGATTCTGACTCGTCG (SEQ ID NO:4) and TTAATGATGATGATGAT GATGGTAACTGGACT-GCTGGGAT (SEQ ID NO:5). Oligonucleotides were synthesized and purified by BioSynthesis, Inc. (Lewisville, Tex.). This PCR product was treated with polynucleotide kinase and T4 DNA polymerase and ligated into the dephosphorylated SmaI site of the expression vector pKK223–3 [Brosius et al. (1984) *Proc. Natl. Acad. Sci. USA* 81:6929–6933]. The ligation mixture was used to transform *E. coli* strain DH5α [supE44 ΔlacU169 φ80lacZ(M15)

hsdR17 recA1 endA1 gyrA96 thi-1 relA1, Ausubel et al., 1989, *Current Protocols in Molecular Biology*, John Wiley & Sons, Inc., New York] to ampicillin resistance. A resulting plasmid clone, pCSRH6-19, complemented the csrA mutation of *E. coli* strain TR1-5BW3414 (ΔlacU169 csrA::kan$^R$), indicating that the plasmid encodes a biologically-active CsrA gene product; the csrA coding region of this plasmid was free of any PCR-generated mutations, determined by DNA sequence analysis. Any strain designation containing the prefix TR1-5 indicates that the wild-type (csrA$^+$) allele has been replaced by the TR1-5 mutant allele (csrA::kan$^R$) by P1vir transduction.

For large scale preparation of CsrA protein, 3 L of an overnight culture of TR1-5BW3414[pCSRH6-19] was used to inoculate a 500 L fermenter containing 350 L LB medium [Miller (1972) *Experiments in Molecular Genetics*, Cold Spring Harbor Laboratory, Cold Spring Harbor, N.Y.] with ampicillin (100 μg/mL). The cells were grown aerobically at 37° C., harvested at late exponential phase, resuspended in 7 L binding buffer (50 mM sodium phosphate pH 8.0, 500 mM NaCl), lysed in a French pressure cell and kept at −80° C. until use (conducted at The Fermentation Facility, University of Alabama, Birmingham). The cell lysate (1 L) was thawed at room temperature, imidazole was added to 20 mM and it was centrifuged at 10,000 g at 4° C. for 30 min. The clear supernatant solution was mixed with 2 mL of pre-washed Ni-NTA resin in binding buffer. After stirring on ice for 2 h, the batch was poured into a glass column and washed first with 40 volumes of binding buffer until the absorbance at 280 nm was less than 0.01, and then with 40 volumes of wash buffer (50 mM sodium phosphate pH 6.0, 500 mM NaCl, 10% glycerol and 20 mM imidazole) until the absorbance was less than 0.01. The CsrA-H6 protein was eluted with a 50 mL linear gradient of imidazole (20 mM to 500 mM) in wash buffer followed by 12 mL of 1 M imidazole in wash buffer. Column fractions containing protein were analyzed by SDS-PAGE (15% gel), and the resolved polypeptides were detected with Coomassie blue staining or by Western immunoblot analysis. The fractions containing electrophoretically-pure protein were pooled, concentrated, dialyzed against 10 mM TrisOAc, pH 8.0, and assayed for total protein. Smith et al.(1985) *Anal Biochem.* 150:76–85. While this method of purification is effective, other methods of protein purification commonly used in the art can be used to purify the CsrA for producing csrB-CsrA combinations of the present invention.

Preliminary small-scale experiments showed that the CsrA-H6 protein was expressed by TR1-5BW3414 [pCSRH6-19], and could be purified in modest yield (0.1 mg/L batch culture) by a single step of affinity chromatography on Ni-NTA agarose. Agarose Ni-NTA affinity resin was purchased from Qiagen (Chatsworth, Calif.). The CsrA-H6 protein preparation used for all of the experiments described here was prepared in large scale from cells grown to late exponential phase in a 500 L fermenter; its electrophoretic properties were indistinguishable from those of smaller-scale preparations. The fractions which were pooled and saved from the affinity matrix contained a single detectable ca. 7 kDa band on SDS PAGE using Coomassie blue staining or Western blot analysis. The yield of CsrA protein from large-scale preparation was approximately 3 mg per 35 L of culture.

In order to authenticate the CsrA-H6 polypeptide of the CsrA-csrB complex and to determine whether it can be covalently modified, N-terminal sequencing, amino acid composition analysis and MALDI TOF mass spectrometry were performed. Fifteen cycles of automated Edman degradation yielded the sequence Met-Leu-Ile-Leu-Thr-Arg-Arg-Val-Gly-Glu(X)-Thr-Leu-Met-Ile-Gly (SEQ ID NO:6), identical to the deduced amino acid sequence of CsrA ([Romeo et al. (1993a)], except for an unexplained minor peak observed in addition to the expected glutamic acid residue at cycle 10. Amino acid analysis was also consistent with the deduced composition of the CsrA protein, with the exception of Gly, which was almost 4-fold higher than expected and was apparently carried over from the transfer buffer, and His was somewhat lower than expected, 4.6 versus 7 residues. MALDI TOF Mass Spectrometry revealed a molecular mass of 7677.7, differing by less than 3 Da from the predicted value of CsrA-H6, indicating that the polypeptide was not covalently modified, except for the deformylation of the N-terminal methionine residue.

N-terminal amino acid sequencing and amino acid composition analysis were performed as follows, although any amino acid sequencing technique known in the art can be used for this purpose. The purified CsrA-H6 complex (1 mg/mL protein in 10 mM TrisOAc) was loaded onto a TFA-activated glass fiber filter and its amino terminal sequence was determined by automated Edman degradation using an ABI 475A gas-phase instrument. Hewick et al. (1981) *J. Biol. Chem.* 256:7990–7997. The reaction cartridge temperature was 50° C. For amino acid composition analysis, 2 μg of concentrated, affinity-purified CsrA-csrB was electrophoresed on a 15% SDS-PAGE and blotted onto PVDF membrane. The membrane was rinsed with water, stained with 0.025% Coomassie blue and 40% methanol, and destained in 50% methanol. The protein was excised, hydrolyzed in 6 N HCl for 24 or 48 hrs and analyzed on an ABI model 420 automated amino acid analyser (Foster City, Calif.) (performed by BioSynthesis, Inc., Lewisville, Tex.).

MALDI TOF mass spectrometry was performed as follows, although any mass spectrometry technique known in the art can be used for this purpose. Mass spectra were acquired using a Vestec LaserTec Research linear instrument (Perceptive Biosystems, Houston, Tex.), employing a nitrogen laser (337 nm), a 1.2 m flight tube and an accelerating voltage of 10 KV. Beavis et al. (1990) *Proc. Natl. Acad Sci. U.S.A.* 87:6873–6877. The mass axis was set by calibration with insulin. Samples were diluted into 0.1% TFA and mixed on the target with an equal vol. of MALDI matrix consisting of a saturated solution of either 3,5-dimethoxy-4-hydroxycinnamic (sinapinic) acid or α-cyano-4-hydroxycinnamic acid dissolved in 40% acetonitrile and 0.1% TFA. Data from 25 to 75 spectra were averaged and assigned using the GRAMS-LaserTec program.

EXAMPLE 2

CsrA-H6 Protein is Bound to csrB RNA in a Discreet Multisubunit Complex

The following experiments demonstrated that CsrA is bound to csrB RNA.

The ultraviolet absorbance spectrum of CsrA-H6 protein purified in Example 1 was found to be typical of nucleic acid instead of protein, i.e. the ratio of absorbance at 260 nm to 280 nm was 2.0. In view of the facts that CsrA modulates glgC mRNA stability in vivo [Liu et al. (1995)] and that the CsrA amino acid sequence contains a putative RNA-binding domain, this nucleic acid was suspected to be RNA. This was confirmed by several approaches. Ribose content of the preparation was quantified by orcinol assay [Schmidt et al. (1945) *J. Biol. Chem.* 181:83–89], and a mass ratio of RNA to protein was determined to be 1.27. Substantial orcinol reactivity relative to absorbance at 260 nm excluded DNA as a major constituent of the preparation, which is not reactive with orcinol. Analysis of the CsrA-H6 preparation by 7.5% native PAGE revealed a single major product which stained with Coomassie blue, Western blot analysis and acridine orange (FIG. 3C, lanes 1 through 3, respectively), indicative of a discreet ribonucleoprotein complex. A ladder of faster-running minor components extending downward from the major component was observed with the most sensitive treatment, Western blotting. The complex yielded red fluorescence with acridine orange treatment, a characteristic of single-stranded RNA, and in contrast to DNA which fluoresces green. McMaster et al. (1977) *Proc. Natl. Acad Sci. U.S.A.* 11:4835–4838. FIG. 3D shows that phenol-purified RNA from the complex consisted of a major RNA band of approximately 350 nucleotides. The native complex was estimated to contain approximately 20 subunits of CsrA-H6 per single-stranded RNA, based upon an approximate size of 350 nucleotides for the RNA, 7.6 kDa for the protein subunit, and a protein:RNA mass ratio of 1.27. DNA and RNA size markers and T4 polynucleotide kinase were purchased from Bethesda Research Laboratories (Gaithersburg, Md.). Attempts to separate the CsrA protein from the RNA under nondenaturing conditions, e.g. strong anion exchange chromatography on MonoQ FPLC, were unsuccessful, suggestive of strong noncovalent interactions within the complex.

Figure 3:
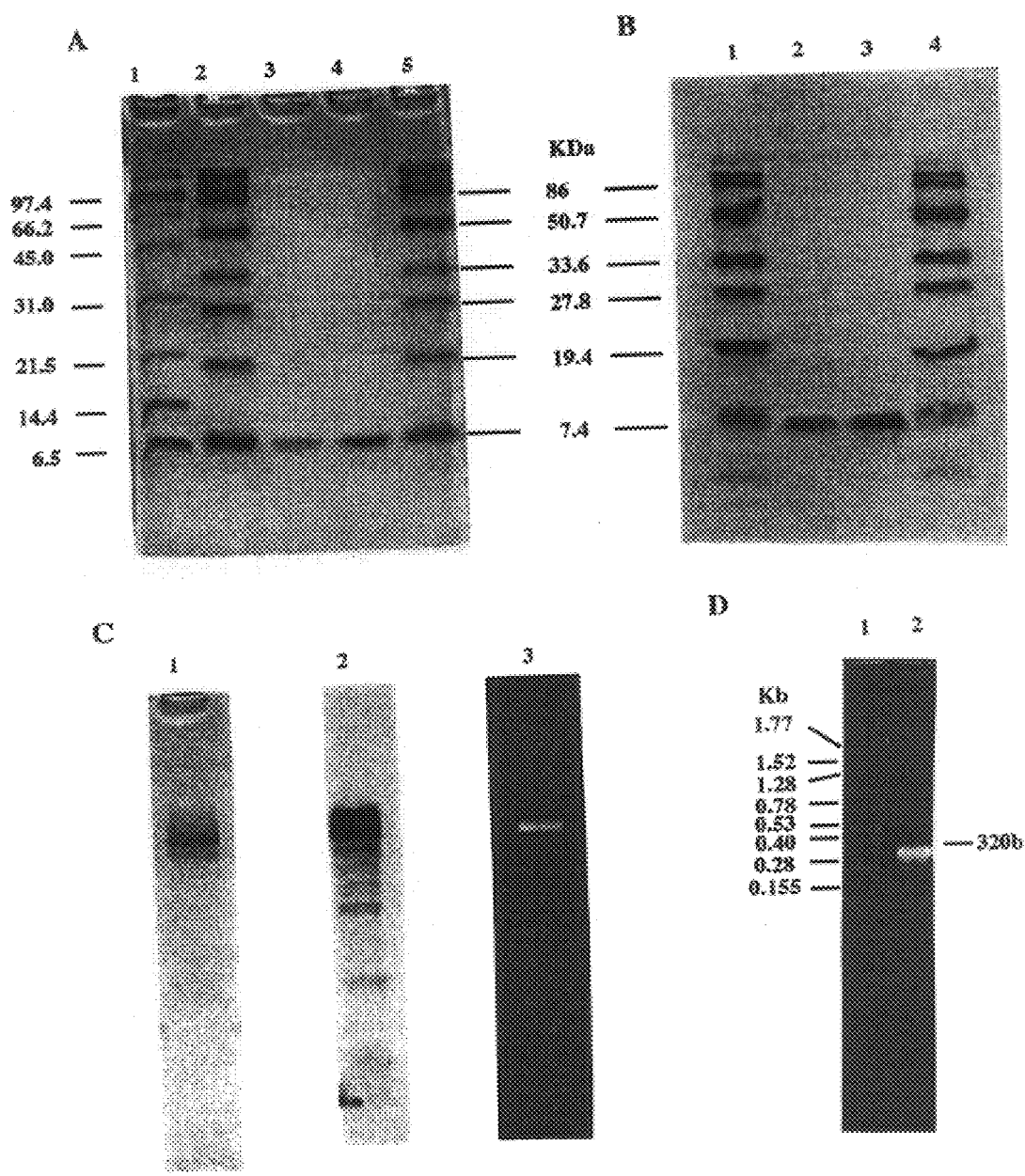
FIGS. 3A–3D illustrates the electrophoretic analysis of a CsrA-csrB complex and its individual CsrA and csrB RNA components.

FIG. 3 shows electrophoretic analyses of CsrA-csrB and its individual CsrA and csrB RNA components. Affinity-purified CsrA-csrB was subjected to denaturing electrophoresis on 15% SDS-PAGE and detected with Coomassie blue or Western blotting in panels A and B, respectively. Panel A, lanes 1 through 5 depict (1) protein molecular weight standards; (2) prestained protein standards; (3) 1 μg CsrA-H6 protein; (4) 2 μg CsrA-H6 protein, and (5) prestained protein standards, respectively. Panel B depicts prestained standards in lanes 1 and 4; and 1 μg or 2 μg of CsrA protein in lanes 2 and 3, respectively. Panel C shows affinity-purified CsrA-csrB (5 μg protein) subjected to 7.5% native PAGE and detected with either Coommassie blue, Western blotting or acridine orange in lanes 1 through 3, respectively. Panel D depicts the analysis of RNA (3 μg) purified from the CsrA-csrB by denaturing agarose gel electrophoresis; RNA ladder size markers are shown in lane 1.

To determine the native molecular mass of CsrA-csrB, affinity-purified CsrA-csrB (4 μg protein) was analyzed by electrophoresis on a series of nondenaturing gels, along with standard proteins (α-lactalbumin, 14.2 kDa; carbonic anhydrase, 29 kDa; bovine serum albumin monomer, 66 kDa; bovine serum albumin dimer, 132 kDa; urease trimer, 272 kDa; and urease hexamer, 545 kDa). These gels contained 5%, 5.5%, 6%, 7%, 8% and 9% acrylamide and their resulting Rf values were calculated as the ratio of migration distance relative to the dye bromophenol blue. The values of 100 [Log (Rf×100)] for each of the proteins was plotted versus gel concentrations as percent, and the logarithm of the negative slope of each curve was then plotted against the logarithm of known molecular mass of each protein to generate a curve from which the molecular mass of CsrA-csrB was estimated. Bryan (1977) *Anal. Biochem.* 78:513–519.

Negative-Staining Electron Microscopy of Native CsrA-csrB Complexes

Figure 4:
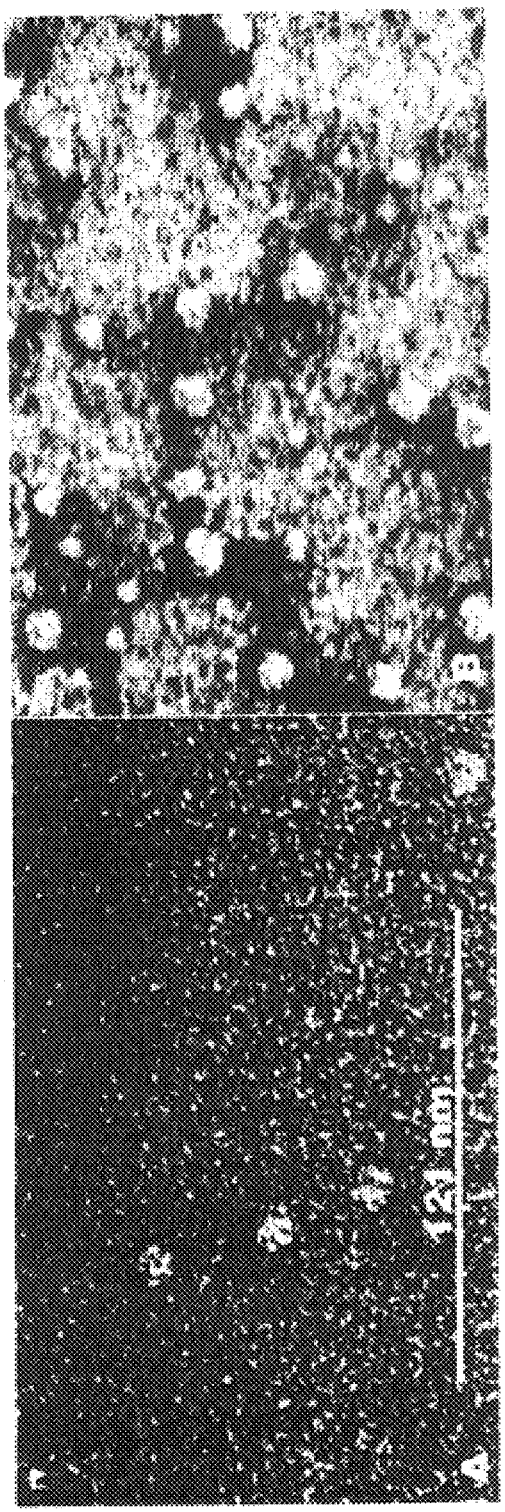
FIG. 4 illustrates the transmission electron microscopy of negatively stained CsrA-csrB complexes.

Transmission electron microscopy of negatively-stained ribonucleoprotein complexes revealed them to be globular in shape and 7.89±0.75 or 7.46±0.12 nm (mean±standard deviation) in diameter, depending upon whether they were treated with EDTA or not, respectively (FIG. 4). Size variability of complexes within each preparation was attributed to some RNA decay during handling. FIG. 4 illustrates transmission electron microscopy of negatively stained CsrA-csrB complexes. (A) Native complex (micrograph); (B) EDTA-treated preparation (digital image).

To perform negative-staining electron microscopy, samples of native complex or complex pretreated with 10 mM EDTA were diluted to 5 (g/mL with 10 mM TrisOAc, pH 8.0 and 2% glutaraldehyde. Glow-discharged formvar-coated grids were touched to 5 μL drops of fixed sample, excess fluid was removed and the grids were floated on 2% uranyl acetate for 2 min. Grids were then blotted with filter paper, air-dried and examined on a Zeiss EM910 instrument. Sogo et al. (1987) *Binding of protein to nucleic acids in Electron Microscopy in Molecular Biology: A Practical Approach* (Sommerville and Scheer, eds.) pp. 61–79, IRL Press. Images were recorded either on Kodak so-163 or digitally with a Dage-MTI Model 72 CCD camera connected to a Scion LG-3 framegrabber board in an Apple Power Macintosh 7200/90 computer. Digital images were used to measure diameter of the complexes using NIH Image and were analyzed statistically with Abacus Statview.

Molecular Mass Determination of CsrA-csrB by Native PAGE

The CsrA-csrB complex was subjected to nondenaturing electrophoresis on 7.5% polyacrylamide gels [Hedrick et al. (1977) *Arch. Bioch. Biophys.* 126:155–164], and was detected by staining protein with Coomassie blue or nucleic acid with acridine orange, which renders single-stranded RNA red and double-stranded DNA green. McMaster et al. (1977) *Proc. Natl. Acad Sci. U.S.A.* 11:4835–4838. Denaturing electrophoresis was carried out using SDS polyacrylamide slab gels [Laemmli (1970) *Nature* 227:680–685] to separate polypeptides denatured with SDS and β-mercaptoethanol according to a method specifically suggested for the analysis of His-tagged proteins (Qiagen, Chatsworth, Calif.).

In western blotting of SDS or nondenaturing gels, proteins were transferred onto 0.2 (m nitrocellulose membrane in transfer buffer (25 mM Tris-HCl, 192 mM Glycine pH 8.3, 20% Methanol; Towbin et al. (1979) *Proc. Natl. Acad. Sci. U.S.A.* 76:4350–4354). The membranes were blocked in 0.3% gelatin and incubated for 4 hours with 2,000-fold diluted rabbit anti-CsrA peptide (Lys-Glu-Val-Ser-Val-His-Arg-Glu-Glu-Ile-Tyr (SEQ ID NO:7); residues 38–48; prepared by Research Genetics, Huntsville, Ala.). After washing three times, the membranes were incubated with sheep-anti-rabbit-horseradish peroxidase conjugate and developed with 4-Cl-N-naphthyl. Sheep-anti-rabbit-horseradish peroxidase, prestained and unstained protein standards for SDS PAGE, PVDF membranes and nitrocellulose membranes were purchased from Bio-Rad (Hercules, Calif.).

Nondenaturing polyacrylamide gel electrophoresis of multimeric proteins on a series of gels with increasing acrylamide concentration is a sensitive and reliable means for estimation of molecular mass, irrespective of charge. Bryan (1977) *Anal. Biochem.* 78:513–519. Since CsrA-csrB was globular upon negative-staining electron microscopy, its size should also be accurately estimated by this approach. Using this approach, the molecular mass of the CsrA-csrB complex was estimated to be 256 kDa. Subtraction of the RNA mass (121 kDa) from this value revealed that there are approximately 18 CsrA subunits per complex by this method, in good agreement with the rough estimation of 20 CsrA subunits per RNA determined by the mass ratio of protein:RNA. This size also corresponds well to the larger structures observed by electron microscopy. Attempts to estimate the size of the complex by sedimentation equilibrium centrifugation were prevented due to precipitation of the complex under the high salt conditions required for the analysis.

Thus, complexes of CsrA protein and csrB polynucleotides had been detected and visualized using a variety of methods, including electrophoresis, Western blotting, electron microscopy, and other techniques.

EXAMPLE 3

Figure 5:
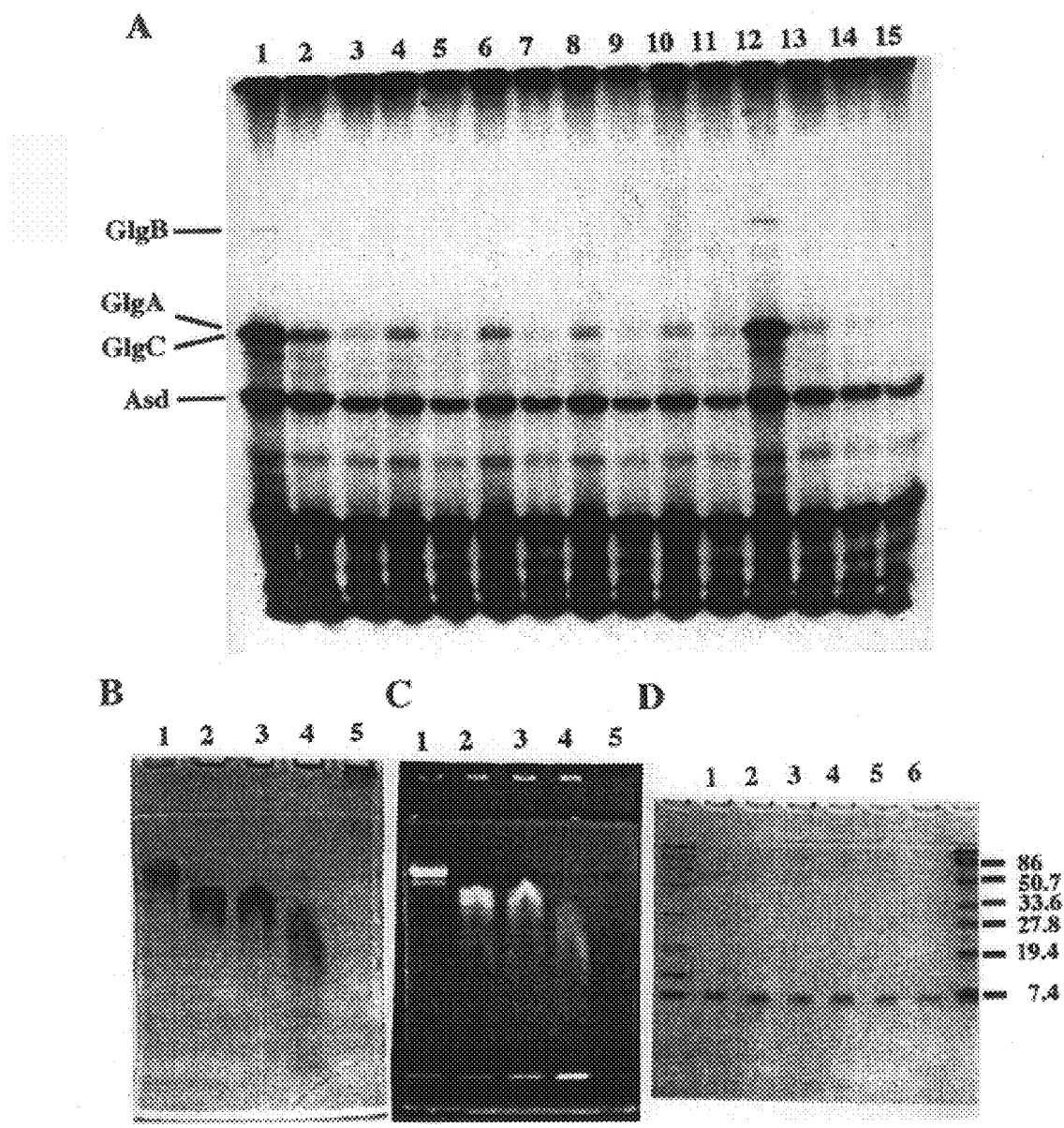
FIGS. 5A–5D illustrate the activity of CsrA-csrB before and after nuclease treatments in S-30 transcriptional translation.

Purified recombinant CsrA is Biologically-Active in the Absence of the RNA Component To determine whether the affinity-purified CsrA-csrB was biologically active, its effects on coupled transcription-translation of glycogen biosynthesis genes were tested in S-30 extracts prepared from TR1-5BW3414 (csrA::kan$^R$), using pOP12 DNA as the genetic template. Romeo et al. (1989); and Liu et al. (1995). TR1-5BW3414 is a derivative of E. coli strain BW3414 (ΔlacU169) (from B. Wanner) carrying csrA::kan$^R$. Preliminary experiments established an appropriate concentration range for testing the CsrA-csrB. FIG. 5 shows that several pOP12-encoded genes were expressed, including the glycogen biosynthetic genes glgB, glgC and glgA, as well as asd, which encodes an enzyme not involved in glycogen biosynthesis, aspartate semialdehyde dehydrogenase (lanes 1 and 12). Addition of CsrA-csrB (0.5 µg protein per 35 µl reaction) specifically and potently inhibited the expression of the glg genes (lanes 2) and in higher concentrations (2.0 µg/reaction; lane 3) their expression was almost undetectable. Decoupling of transcription and translation in these reactions using rifampin showed that this specific inhibition of glg gene occurs posttranscriptionally, in agreement with the conclusion that CsrA facilitates the decay of glg mRNA in vivo. Liu et al. (1995).

FIG. 5 illustrates activity of CsrA-csrB before and after nuclease treatments in an S-30 transcription-translation system. CsrA-csrB RNA complex (25 µg protein) was treated with micrococcal nuclease, followed by nuclease inactivation with EGTA or was treated with RNase A followed by affinity repurification. It was then tested for its ability to modulate in vitro transcription-translation of glycogen biosynthesis genes (panel A), for its mobility on 7.5% native PAGE stained with Coomassie blue or acridine orange, respectively (panels B and C, respectively), or for the mobility of the denatured polypeptide subunits on 15% SDS-PAGE followed by Coomassie blue staining (panel D). Specific treatment regimens included: (1) mock-treatment without micrococcal nuclease; (2) treatment with 100 U micrococcal nuclease but without CaCl$_2$; (3) treatment with 100 U micrococcal nuclease and 1 mM CaCl$_2$; (4) treatment with 500 U micrococcal nuclease and 1 mM CaCl$_2$; (5) treatment with RNase A and repurification. In panel A, S-30 reactions were conducted in the presence of either no CsrA-H6 protein (lanes 1 and 12), 0.5 µg CsrA-H6 protein (lanes 2, 4, 6, 8, 10, 13), 1.0 µg CsrA-H6 (lane 14) or 2.0 µg CsrA-H6 protein (lanes 3, 5, 7, 9, 11, 15), subjected to no treatment (2, 3), regimen 1 (lanes 4, 5); regimen 2 (lanes 6, 7); regimen 3 (lanes 8, 9); regimen 4 (lanes 10, 11) regimen 5 (lanes 13, 14 and 15). The positions of unlabeled standards of glycogen branching enzyme (GlgB), ADPglucose pyrophosphorylase (GlgC), glycogen synthase (GlgA) were determined by Coomassie blue staining and aspartate semialdehyde dehydrogenase (Asd) was identified by its mobility (13). In panels B and C, CsrA-csrB subjected to each of the five treatment regimens is shown in lanes 1 through 5, respectively. In panel D, untreated CsrA-csrB complex and the five treated preparations are shown in lanes 1 through 6, respectively.

Effects of the CsrA Gene product on the expression of glycogen biosynthesis genes encoded by plasmid pOP12 (glgB, glgC, and glgA) were examined in transcription-translation reactions using an S-30 extract prepared from strain TR-15BW3414 (csrA::kan$^R$) and containing 100 µM cAMP and 1 µg of cAMP receptor protein. The methodology has been previously described in detail. Romeo et al. (1989); and Liu et al. (1995).

The requirement of the RNA component of the CsrA-csrB complex for biological activity was tested by treatment of the complex with micrococcal nuclease followed by EGTA inactivation of this enzyme, or with RNase A treatment followed by affinity repurification of the CsrA protein. RNase A, high quality imidazole and native protein molecular weight markers were purchased from Sigma Chemical Co. (St. Louis, Mo.).

RNA-free CsrA was prepared by treating CsrA-csrB (0.6 mg protein) with DNase-free RNase A (10 µg/mL) in 5 mM EDTA and 10 mM Tris acetate, pH 8.0 at 37° C. for 30 min. After dialyzing at 4° C. overnight against two changes of binding buffer (50 mM sodium phosphate pH 8.0, 500 mM NaCl and 20 mM imidazole), the protein was separated from the reaction mixture by binding to a Ni-NTA spin column (Qiagen, Chatsworth, Calif.) and elution with 1 M imidazole in binding buffer. The eluate was dialyzed overnight against two changes of 10 mM TrisOAc pH 8.0 and concentrated to 0.4 mg/mL in an Amicon stirred cell (Amicon Inc., Beverly, Mass.). Alternatively, RNA of the CsrA-csrB was hydrolyzed with the Ca++ dependent enzyme micrococcal nuclease, which was inactivated using EGTA.

As shown by native PAGE (FIG. 5B and C) micrococcal nuclease treatments yielded faster-migrating CsrA-csrB complexes, indicative of RNA degradation, while the CsrA-H6 protein was not altered, as shown by SDS PAGE (panel D). RNase A treatment followed by affinity purification yielded CsrA-H6 protein essentially free of RNA. On native PAGE, the RNA-free protein migrated slower than the original csrB complexes and was observed near the top of the stacking and running, gels, consistent with the fact that this protein is somewhat basic, and suggestive of possible protein aggregation (panels B and C). No acridine orange staining was observed in this region of the native gels. The mobility of the RNA-free protein on SDS PAGE was unaltered (panel D). The protein remained fully-active in specific genetic regulation under all treatment conditions. In fact, Micrococcal nuclease treated or RNA-free CsrA-H6 preparations were somewhat more inhibitory to glg gene expression than was the CsrA-csrB complex. Clearly, the RNA component of the CsrA-csrB complex was not required for the biological activity of CsrA in vitro. Furthermore, these data strongly suggest that csrB RNA antagonizes the activity of CsrA.

EXAMPLE 4 cDNA Cloning and Sequencing of csrB RNA

Molecular characterization of the purified RNA component of the CsrA-csrB complex was accomplished by preparing cDNA clones, determining the nucleotide sequence from 14 different cDNA clones, and searching databases for homologous genes. Database searches were performed using BLAST analysis [Altschul et al. (1990) *J. Mol. Biol.* 215:403–410] via the internet services at the National Center for Biotechnology Information.

This approach revealed that the RNA was transcribed from a locus in the 64 min region of the *E. coli* K-12 genome, which had been previously sequenced (G. Plunkett, Nucleotide sequence accession no. U29581 National Center for Biotechnology Information), but had not been otherwise studied. The gene encoding this RNA was designated as csrB.

FIG. 1 (SEQ ID NO:1) illustrates the nucleotide sequence of csrB of *E. coli* K-12 (upper case). Underlined sequences include the termination codon of the nearby syd gene of *E. coli* [Shimoike et al. (1995) *J. Biol. Chem.* 270: 5519–5526] and the inverted repeats of the putative rho independent termination sites of csrB. The characteristic highly repeated motifs are underlined and in bold. The nucleotide positions of 5' and 3' ends of csrB cDNA clones showed some variability, attributed to nucleolytic attack during purification of the CsrA-csrB native complex; the 3'- and 5'-most terminal nucleotides present among 14 different cDNA clones (nucleotides 221 and 516) are marked with asterisks. The region of DNA which was amplified by PCR and cloned to yield pCSRB-SF and pCSRB-SR (residues 170 to 654) is also marked with asterisks.

The csrB gene is immediately downstream from and in the same orientation as syd, which encodes a protein that interacts with the SecY gene product, a component of the protein secretion apparatus. Shimoike et al. (1995). No significant open reading frames were found within csrB, indicating that csrB does not function as a mRNA. At the 3' end of csrB is a perfect 10 bp stem and loop sequence followed immediately by UUUUUUUUAUU (SEQ ID NO:8), characteristic of a rho-independent transcription terminator. Platt (1986) *Ann. Rev. Biochem.* 55:339–372. No typical promoter sequence is present between csrB and the 3' end of syd.

A highly repeated element potentially involved in binding to CsrA. In order to identify the sites in csrB which could interact with 18 CsrA subunits to form the observed CsrA-csrB complex, we scanned the RNA sequence for highly repeated elements. Located within the csrB sequence are numerous imperfect repeats of the consensus sequence 5'-CAGGA(U,C,A)G-3' (FIG. 1 (SEQ ID NO:1)).

Secondary structure predictions for csrB RNA. The entire nucleotide sequence was folded with the program STAR 4.1, developed by F. H. D. van Batenburg, running on a Macintosh PowerMac 7500 platform. STAR arrives at a secondary structural prediction using one of three algorithms (sequential, stochastic or genetic folding algorithms) by simulating the folding pathway of an RNA from the 5' end of the molecule, rather than by necessarily calculating the most stable structure predicted by the RNA sequence. The results presented here were obtained with a stochastic algorithm [Gultyaev (1991) *Nucl. Acids Res.* 19:2489–2494] using the default nearest neighbor energy rules, an increment value of 25 nucleotides and a population size of 10. Structure predictions obtained with STAR were rendered by LoopDloop (obtained from D. Gilbert, Indiana U.). Secondary structural models generated by the sequential folding algorithm [Abrahams et al. (1990) *Nucl. Acids Res.* 18:3035–3044] were substantially similar to those obtained with the stochastic algorithm. Nucleotides 1–217 and 295–360 were folded identically by both algorithms; nucleotides 218–294 were folded into 4 stem structures which were distinct in each case. Models generated with a genetic algorithm [Gultyaev et al. (1995) *J. Mol. Biol.* 250:37–51] were also similar to the stochastic model, except that two sets of long-range interactions between single-stranded regions involving nucleotides 64–66 basepairing with 315–317 and 118–121 with 270–273 were predicted. In the absence of other phylogenetic or chemical modification data these three models cannot be distinguished from one another.

When RNA secondary structure was predicted, these sequences were found predominantly in single stranded regions of the molecule. Most strikingly, approximately half of the sequences were consistently localized to the loop regions of characteristic 5-member hairpin-loops distributed throughout the RNA, while others were consistently not in such regions (FIG. 2 (SEQ ID NO:2)). These hairpin-loops are closed by the 5'-C:G-3' base pair of the consensus sequence, which itself forms the terminal base pair of the non-conserved short stem. The sequence 5'-CAGGAUG is the most prevalent variant of the loop motif. Excluding the apparent Rho-independent terminator, all except two of the predicted stem-loop structures of csrB contain the conserved sequence elements.

FIG. 2 (SEQ ID NO:2) illustrates a predicted secondary structure prediction for csrB RNA. The structure prediction shown was generated using a stochastic folding algorithm as described herein. The repeated sequence elements are numbered 1 to 18. Many sequence elements conserve the 5' and 3' bases of the seven nucleotide element so that they can basepair with one another (5'-C and 3'-G). 16 of 18 elements are predicted to reside in single-stranded regions, with 10 of 12 heptanucleotide sequences which conserve the 5' and 3' bases are found specifically in a five-nucleotide hairpin loop structure closed by a C-G basepair.

EXAMPLE 5

Database Searches for csrB Homologs

An apparent csrB homolog in *E. carotovora* activates genes which are repressed by the csrA homolog, rsmA. Database searches also identified a sequence homologous to csrB in the plant pathogen *E. carotovora*. (FIG. 9 (SEQ ID NO:3)).

FIG. 9 (SEQ ID NO:3) illustrates a nucleotide sequence comparison of csrB of *E. coli* K-12 (upper case) and the aepH region of *Erwinia carotovora* (lower case). Underlined sequences include the termination codon of the syd gene of *E. coli* [Shimoike et al. (1995)] and the inverted repeats of the putative rho independent termination sites of csrB and aepH. The characteristic highly repeated motifs of both species are underlined and bolded. The previously proposed Shine Dalgarno sequence, initiation codon, and termination codon of aepH are shown by double underlines. Murata et al. (1994). The nucleotide positions of 5' and 3' ends of csrB cDNA clones showed some variability, attributed to nucleolytic attack during purification of the CsrA-csrB native complex; the 3'- and 5'-most terminal nucleotides present among 14 different cDNA clones (nucleotides 221 and 516) are marked with asterisks. The region of DNA which was amplified by PCR and cloned to yield pCSRB-SF and pCSRB-SR (residues 170 to 654) is marked with asterisks. Limit points of upstream deletions in *Erwinia carotovora* which either inactivated (−) or did not alter the activity of this region (+) with respect to exoenzyme production [Murata et al. (1994)] are also indicated.

This region of *E. carotovora* was previously found to activate the expression of the same extracellular virulence proteins which are repressed by rsmA, the csrA homolog of this species. Cui et al. (1995). A 141 nucleotide open reading frame initiating with the codon GTG was proposed to encode a protein responsible for the observed effects, and was called aepH for activator of extracellular proteins. Murata et al. (1994). However, no evidence showed that aepH is actually translated, and this small reading frame itself is not conserved in *E. coli*. Rather, the *E. coli* and *E. carotovora* regions both contain the highly repeated consensus sequences. As in *E. coli*, the *E. carotovora* repeated sequences are also predicted to be predominantly found in single stranded regions and in loops of stem and loop structures of the RNA encoded by this region (not shown). Murata and coworkers had previously recognized these unusual repeated sequences, and had found that they were significant for the function of this region, since mutations and deletions which were well upstream from the proposed aepH reading frame but among or immediately upstream from the repeated elements inactivated the gene. Murata et al. (1994).

Although csrA homologs are now known from a variety of eubacterial species, including *H. influenzae*, the entire genome of which has been sequenced [Fleischmann et al. (1995) *Science* 269:496–512], no csrB homolog was located in the *H. influenzae* sequence or elsewhere by nucleotide database searches. This indicates that either other bacterial species lack csrB or more likely that the sequence of csrB RNA is not highly conserved beyond the level of the bacterial family. The latter is a direct prediction of the hypothesis that the variably-spaced repeated elements of csrB RNA are essential for its function, and not a protein coding sequence or an overall RNA secondary structure as occurs in ribozymes.

Examination of the glgC message and mRNA's of other CsrA-regulated genes did not reveal the repeated stem-loop structures. Nevertheless, the Shine-Dalgarno sequence of glgC (AAGGAGU) is located within the cis-acting region which mediates CsrA regulation [Liu et al. (1995)] and contains the central portion of the repeat within a predicted single-stranded region.

EXAMPLE 6

Overexpression of csrB RNA Antagonizes CsrA Activity

Figure 6:
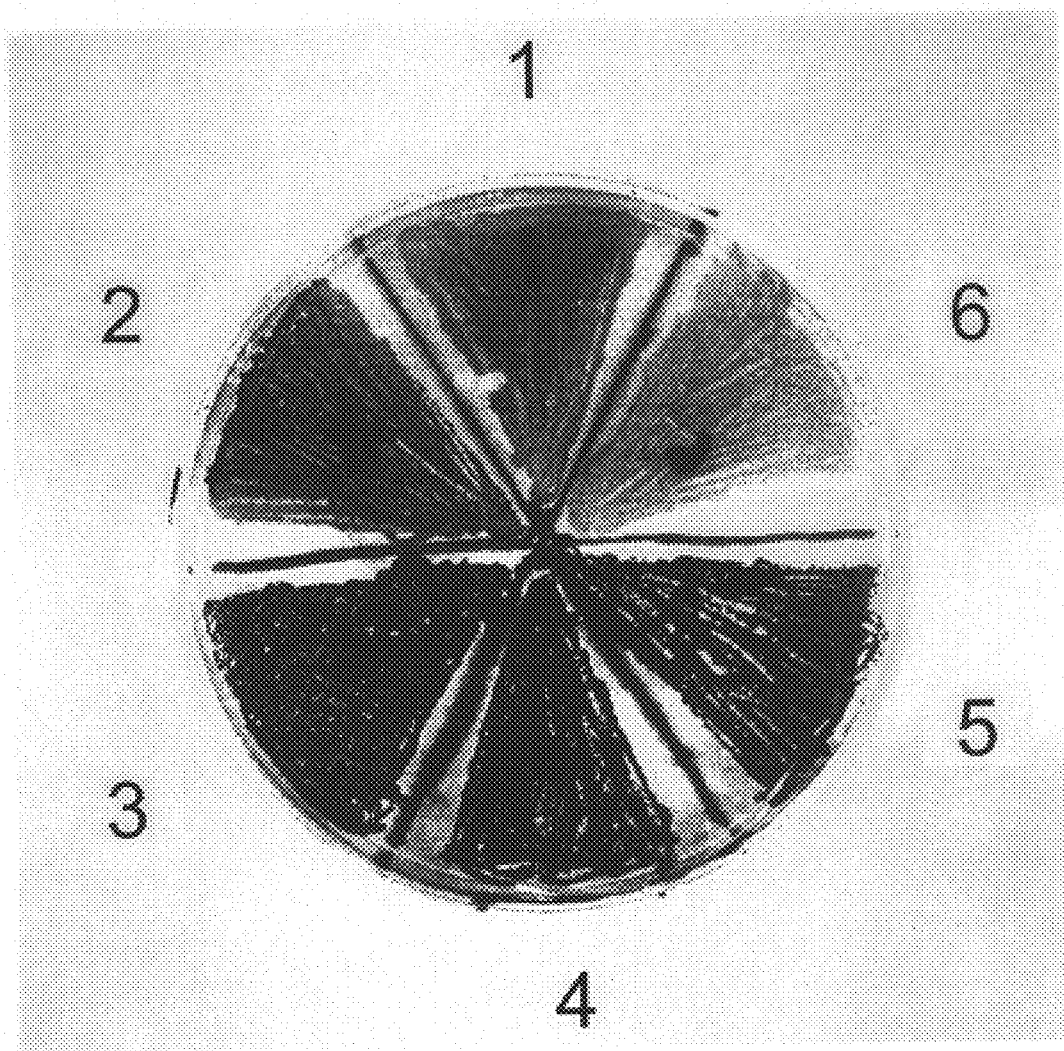
FIG. 6 illustrates overexpression of csrB on glycogen accumulation in E. coli.

Using PCR, a 0.5 Kb region containing an almost minimal csrB gene was amplified and subsequently cloned. FIG. 6 shows that the clones in which csrB can be expressed via the lacZ promoter of the vector, e.g. pCSRB-SF, strongly enhanced glycogen accumulation by *E. coli*, while plasmids in which the csrB gene is oriented in the opposite direction, e.g. pCSRB-SR, had a weak or negligible stimulatory effect.

FIG. 6 illustrates that overexpression of csrB stimulates glycogen accumulation in *E. coli*. Isogenic strains which vary in either csrA or csrB genes were streaked onto Kornberg medium containing 1% glucose and 100 mg/mL of ampicillin, grown overnight and stained with iodine vapor to detect intracellular glycogen. Strain identities: 1, BW3414 [pUC19] (csrA$^+$csrB$^+$); 2, BW3414[pCSRB-SR] (csrA$^+$, csrB$^+$cloned in pUC18, opposite orientation relative to lac promoter); 3, BW3414[pCSRB-SF] (csrA$^+$, csrB cloned in pUC19, in same orientation as lac promoter); 4, TR1-5BW3414[pCSRB-SF] (csrA::kan$^R$, csrB cloned in same orientation as lac promoter); 5; TR1-5BW3414[pUC19] (csrA::kan$^R$); 6; TR1-5BW3414[pCSR10] (csrA cloned into pUC19).

To construct pCSRB-SF and pCSRB-SR, the csrB gene was amplified from λDD628 DNA by PCR using the oligonucleotide primers GTAAGCGCC-TTGTAAGACTTC (SEQ ID NO:9) and CTGGAGACGAACGCGGTCATG (SEQ ID NO:10), and the PCR product was treated with T4 DNA polymerase and polynucleotide kinase, and cloned into the SmaI site of pUC18 [Yanish-Perron et al. (1985) *Gene* 33:103–119] to yield pCSRB-SR. Subsequently, pCSRB-SR was treated with EcoRI and BamHI and the insert DNA was subcloned into pUC19 to yield the plasmid clone pCSRB-SF, which was later sequenced for verification.

Glycogen Staining. Effects of the *E. coli* csrA and csrB genotypes on glycogen levels were observed by staining colonies with iodine vapor. Liu et al. (1995).

These results demonstrated that multiple copies of the csrB gene in the cell do not simply bind to (or titrate-out) a DNA-binding protein inhibitor of glycogen synthesis, but that expression of csrB RNA is required for its effects on glycogen. The effect of pCSRB-SF (in which csrB was cloned into pUC19 in the same orientation as the lac promoter) on glycogen levels was not as strong as the TR1-5 csrA::kan$^R$ mutation, which causes cells to accumulate more than 20-fold higher levels of glycogen. Romeo et al. (1993a); and Yang et al. (1996) *J. Bacteriol.* 178:1012–1017. The introduction of pCSRB-SF into a strain which was defective in csrA, TR1-5BW3414, did not alter its glycogen levels (FIG. 6). Several *E. coli* strains which are wild type for csrA were transformed with PCSRB-SF (BW3414, DH5α, JM101, and *E. coli* B) and in each case the transformants accumulated elevated levels of glycogen. Furthermore, the multicopy plasmid clones pAK671 and pAK672, which encode csrB homologs aepH* and aepH$^+$ of *Erwinia carotovora* [Murata et al. (1994)], also stimulated glycogen accumulation in *E. coli*, indicating that csrB and aepH are functionally equivalent.

These results clearly indicate that overexpression of csrB RNA antagonized CsrA activity, results in an alteration in metabolic pathways and increased production of a metabolite.

All publications and patent applications cited in this specification are incorporated herein by reference to the same extent as if each individual publication or patent application was specifically and individually indicated to be incorporated by reference.

Although the foregoing invention has been described in some detail by way of illustration and example for purposes of clarity and understanding, it will be apparent to those skilled in the art that certain modifications can be practiced. Therefore, the description and examples should not be construed as limiting the scope of the invention, which is delineated by the appended claims.

What is claimed is:

1. A method of altering the metabolism or structural or functional properties of a cell comprising altering genetic expression of csrB.

2. The method according claim 1, wherein a result of altered genetic expression of csrB is a change in the level of production of a metabolic compound, and wherein the level of production is at least partially reguated by CsrA.

3. The method according claim 1, wherein a result of altered genetic expression of csrB is a change in glycogen biosynthesis or gluconeogenesis.

4. The method according to claim 1, wherein expression of the csrB gene is increased.

5. The method according to claim 1, wherein expression of the csrB gene is decreased.

6. The method according to claim 1, wherein expression of the csrB gene is under inducible control.

7. A method of modulating the level of production of a metabolic compound, wherein the level of production is at least partially controlled by CsrA, comprising the steps of:

(a) introducing a vector comprising a csrA gene and a csrB gene into a host cell, wherein the csrA gene and the csrB gene are controlled by different inducible promoters; and (b) raising the level of production of the metabolic compound by inducing expression of csrB.

8. A method according to claim 7 further comprising the step:

(c) decreasing the level of production of the metabolic compound by inducing expression of CsrA.

* * * * *